US007448653B2

(12) United States Patent
Jensen et al.

(10) Patent No.: US 7,448,653 B2
(45) Date of Patent: Nov. 11, 2008

(54) FEMALE CONNECTOR FOR RELEASABLE COUPLING WITH A MALE CONNECTOR DEFINING A FLUID CONDUIT

(75) Inventors: Jeffrey P. Jensen, Fort Collins, CO (US); James D. Pisula, Jr., Fort Collins, CO (US); Ralph E. Burns, Louisville, CO (US); Raymond Townsend, Johnstown, CO (US); Richard W. Cairns, Longmont, CO (US)

(73) Assignee: Value Plastics, Inc., Fort Collins, CO (US)

( * ) Notice: Subject to any disclaimer, the term of this patent is extended or adjusted under 35 U.S.C. 154(b) by 11 days.

(21) Appl. No.: 11/149,624

(22) Filed: Jun. 10, 2005

(65) Prior Publication Data

US 2008/0007051 A1    Jan. 10, 2008

(51) Int. Cl.
*F16L 37/00* (2006.01)
(52) U.S. Cl. ................... 285/307; 285/305; 285/308; 604/533
(58) Field of Classification Search ................ 285/305, 285/307–308, 317; 604/284, 533–536
See application file for complete search history.

(56) References Cited

U.S. PATENT DOCUMENTS

| 163,261 A | 5/1875 | Ruppenthal |
| 185,896 A | 1/1877 | Curtis |
| 187,982 A | 3/1877 | Pirsson et al. |
| 235,580 A | 12/1880 | Smith et al. |
| 327,509 A | 10/1885 | Aldridge |
| 465,868 A | 12/1891 | List |
| 584,008 A | 6/1897 | Munson |
| 725,421 A | 4/1903 | Dinkins |
| 727,982 A | 5/1903 | Ludwig |
| 874,957 A | 12/1907 | Godley |
| 884,461 A | 4/1908 | Browne |
| 909,131 A | 1/1909 | Antic |

(Continued)

OTHER PUBLICATIONS

Brochure, "Precision Components", Value Plastics, Inc., 2002.

*Primary Examiner*—Aaron M Dunwoody
*Assistant Examiner*—Fannie Kee
(74) *Attorney, Agent, or Firm*—Dorsey & Whitney LLP

(57) ABSTRACT

A female connector for releasable coupling with a male connector is disclosed herein. The male connector defines a fluid conduit and includes a male end adapted to be received within the female connector. The male end includes a coupling feature. The female connector comprises an opening, a collet finger, and an actuation element. The opening is adapted to guide the male connector along a first line of action as the male connector passes into the opening to be received within the female connector. The collet finger includes an engagement feature adapted to engage the coupling feature of the male end and displace along a second line of action generally normal to the first line of action. The actuation element is adapted to displace along a third line of action generally normal to the first and second lines of action in order to disengage the engagement feature from the coupling feature of the male end. When the engagement feature is engaged with the coupling feature, the fluid conduit of the male connector is held in fluid communication with a fluid conduit of the female connector.

6 Claims, 39 Drawing Sheets

U.S. PATENT DOCUMENTS

| | | |
|---|---|---|
| 951,889 A | 3/1910 | Teuer |
| 1,029,819 A | 6/1912 | Nylander |
| 1,033,187 A | 7/1912 | Metzger |
| 1,039,354 A | 9/1912 | Bonadio |
| 1,077,417 A | 11/1913 | McCracken |
| 1,078,112 A | 11/1913 | Storm |
| 1,193,446 A | 8/1916 | Wells |
| 1,239,345 A | 9/1917 | Brown |
| 1,255,847 A | 2/1918 | Arkin |
| 1,259,684 A | 3/1918 | Vinten |
| 1,489,310 A | 4/1924 | Critchlow |
| 1,578,504 A | 3/1926 | Bronson et al. |
| 1,587,079 A | 6/1926 | Machino |
| 1,767,073 A | 6/1930 | Ingold |
| 1,863,360 A | 6/1932 | Weatherhead |
| 1,950,947 A | 3/1934 | Mulroyan |
| 2,023,428 A | 12/1935 | Liebhardt |
| 2,056,524 A | 10/1936 | Johnson |
| 2,066,473 A | 1/1937 | Jorgensen |
| 2,097,628 A | 11/1937 | Liebhardt |
| 2,099,335 A | 11/1937 | Hansen |
| 2,139,745 A | 12/1938 | Goodall |
| 2,147,355 A | 2/1939 | Scholtes |
| 2,159,116 A | 5/1939 | Zacharias |
| 2,211,147 A | 8/1940 | Miller |
| 2,257,321 A | 9/1941 | Arnold |
| 2,263,293 A | 11/1941 | Ewald |
| 2,340,119 A | 1/1944 | Graham |
| 2,346,445 A | 4/1944 | Merker et al. |
| 2,352,728 A | 7/1944 | Merker et al. |
| 2,429,782 A | 10/1947 | Versoy |
| 2,432,946 A | 12/1947 | Theunissen |
| 2,470,800 A | 5/1949 | Ashton |
| 2,479,499 A | 8/1949 | Le Clair |
| 2,500,720 A | 3/1950 | Van der Heem |
| 2,507,536 A | 5/1950 | Goodson |
| 2,516,583 A | 7/1950 | Moore |
| 2,535,740 A | 12/1950 | Knopp |
| 2,577,009 A | 12/1951 | Frantz |
| 2,626,974 A | 1/1953 | Howard et al. |
| 2,630,131 A | 3/1953 | Snyder |
| 2,661,018 A | 12/1953 | Snyder |
| 2,701,147 A | 2/1955 | Summerville |
| 2,753,195 A | 7/1956 | Palmer |
| 2,774,616 A | 12/1956 | Dodd et al. |
| 2,790,571 A | 4/1957 | Flaith et al. |
| 2,864,628 A | 12/1958 | Edleson |
| 2,915,325 A | 12/1959 | Foster |
| 2,926,934 A | 3/1960 | Gill |
| 2,931,668 A | 4/1960 | Baley |
| 2,937,892 A | 5/1960 | Prescott, Jr. |
| 2,948,553 A | 8/1960 | Gill et al. |
| 2,991,090 A | 7/1961 | De Cenzo |
| 3,017,203 A | 1/1962 | Macleod |
| 3,037,497 A | 6/1962 | Roberson |
| 3,073,342 A | 1/1963 | Magorien |
| 3,078,068 A | 2/1963 | Romney |
| D196,473 S | 10/1963 | Hill |
| 3,124,157 A | 3/1964 | Krzewina |
| 3,171,196 A | 3/1965 | Helitas |
| 3,217,771 A | 11/1965 | Beall et al. |
| 3,227,380 A | 1/1966 | Pinkston |
| 3,237,974 A | 3/1966 | Press |
| 3,245,703 A | 4/1966 | Manly |
| 3,276,799 A | 10/1966 | Moore et al. |
| 3,279,497 A | 10/1966 | Norton et al. |
| 3,314,696 A | 4/1967 | Ferguson et al. |
| D209,166 S | 11/1967 | Hunt |
| D209,168 S | 11/1967 | Hunt |
| 3,352,576 A | 11/1967 | Thomas |
| 3,382,892 A | 5/1968 | Cerbin |
| 3,403,930 A | 10/1968 | Bernier |
| 3,448,760 A | 6/1969 | Cranage |
| 3,450,424 A | 6/1969 | Calisher |
| 3,512,808 A | 5/1970 | Graham |
| 3,523,701 A | 8/1970 | Graham |
| 3,538,940 A | 11/1970 | Graham |
| 3,545,490 A | 12/1970 | Burrus |
| 3,550,626 A | 12/1970 | Daniels et al. |
| 3,560,027 A | 2/1971 | Graham |
| 3,563,265 A | 2/1971 | Graham |
| 3,574,314 A | 4/1971 | Quercia |
| 3,588,149 A | 6/1971 | Demler |
| 3,596,933 A | 8/1971 | Luckenbill |
| 3,599,843 A | 8/1971 | Johnston |
| 3,600,917 A | 8/1971 | Krock |
| 3,690,336 A | 9/1972 | Drum |
| 3,712,583 A | 1/1973 | Martindale et al. |
| 3,750,238 A | 8/1973 | Tanner |
| 3,815,887 A | 6/1974 | Curtis et al. |
| 3,817,561 A | 6/1974 | Kay |
| 3,876,234 A | 4/1975 | Harms |
| 3,889,710 A | 6/1975 | Brost |
| 3,899,200 A | 8/1975 | Gamble |
| 3,921,656 A | 11/1975 | Meisenheimer, Jr. et al. |
| 3,979,934 A | 9/1976 | Isenmann |
| 3,990,674 A | 11/1976 | Schattenberg |
| 4,025,049 A | 5/1977 | Schmidt |
| 4,039,213 A | 8/1977 | Walters |
| 4,072,330 A | 2/1978 | Brysch |
| 4,099,748 A | 7/1978 | Kavick |
| 4,129,145 A | 12/1978 | Wynn |
| 4,142,546 A | 3/1979 | Sandau |
| D252,470 S | 7/1979 | Pawlak |
| 4,181,149 A | 1/1980 | Cox |
| D255,145 S | 5/1980 | Nederman |
| 4,220,360 A | 9/1980 | Jacek et al. |
| D258,526 S | 3/1981 | Nederman |
| D259,278 S | 5/1981 | McCaw |
| 4,271,865 A | 6/1981 | Galloway et al. |
| 4,287,644 A | 9/1981 | Durand |
| 4,296,949 A | 10/1981 | Muetterties et al. |
| 4,319,774 A | 3/1982 | Kavick |
| 4,330,010 A | 5/1982 | Drescher et al. |
| 4,330,142 A | 5/1982 | Paini |
| 4,331,175 A | 5/1982 | Brake et al. |
| 4,331,177 A | 5/1982 | Makishima |
| 4,340,200 A | 7/1982 | Stegmeier |
| 4,345,786 A | 8/1982 | Egert |
| 4,346,703 A | 8/1982 | Dennehey |
| 4,351,351 A | 9/1982 | Flory et al. |
| 4,366,816 A | 1/1983 | Bayard et al. |
| 4,393,548 A | 7/1983 | Herb |
| 4,397,442 A | 8/1983 | Larkin |
| 4,434,121 A | 2/1984 | Schaper |
| 4,436,125 A | 3/1984 | Blenkush |
| 4,437,689 A | 3/1984 | Goebel et al. |
| 4,439,188 A | 3/1984 | Dennehey |
| 4,458,719 A | 7/1984 | Strybel |
| 4,500,118 A | 2/1985 | Blenkush |
| 4,527,745 A | 7/1985 | Butterfield et al. |
| 4,541,457 A | 9/1985 | Blenkush |
| 4,541,657 A | 9/1985 | Smyth |
| D282,962 S | 3/1986 | Gerber |
| 4,603,888 A | 8/1986 | Goodall et al. |
| 4,613,112 A | 9/1986 | Phlipot et al. |
| 4,632,436 A | 12/1986 | Kimura |
| 4,658,326 A | 4/1987 | Clark et al. |
| 4,694,544 A | 9/1987 | Chapman |
| 4,699,298 A | 10/1987 | Grant et al. |
| 4,703,957 A | 11/1987 | Blenkush |
| 4,706,847 A | 11/1987 | Sankey et al. |
| 4,712,280 A | 12/1987 | Fildan |
| 4,738,401 A | 4/1988 | Filicicchia |

| | | | | | | |
|---|---|---|---|---|---|---|
| 4,753,268 A | 6/1988 | Palau | | 5,911,367 A | 6/1999 | McInerney |
| 4,776,067 A | 10/1988 | Sorensen | | 5,911,403 A | 6/1999 | deCler et al. |
| 4,790,567 A | 12/1988 | Kawano et al. | | 5,911,404 A | 6/1999 | Cheng |
| 4,790,569 A | 12/1988 | Chaffee | | 5,930,424 A | 7/1999 | Heimberger et al. |
| 4,792,115 A | 12/1988 | Jindra et al. | | 5,941,577 A | 8/1999 | Musellec |
| 4,793,637 A | 12/1988 | Laipply et al. | | 5,957,898 A | 9/1999 | Jepson et al. |
| D300,361 S | 3/1989 | Tokarz | | 5,964,485 A | 10/1999 | Hame et al. |
| 4,827,921 A | 5/1989 | Rugheimer | | 5,975,489 A | 11/1999 | deCler et al. |
| 4,863,201 A | 9/1989 | Carstens | | D419,861 S | 2/2000 | Khokhar |
| 4,896,402 A | 1/1990 | Jansen et al. | | 6,024,124 A | 2/2000 | Braun et al. |
| 4,900,065 A | 2/1990 | Houck | | 6,029,701 A | 2/2000 | Chaffardon et al. |
| 4,903,995 A | 2/1990 | Blenkush et al. | | 6,032,691 A | 3/2000 | Powell et al. |
| 4,923,228 A | 5/1990 | Laipply et al. | | D422,487 S | 4/2000 | Khokhar |
| 4,934,655 A | 6/1990 | Blenkush et al. | | 6,050,297 A | 4/2000 | Ostrowski et al. |
| 4,935,992 A | 6/1990 | Due | | 6,076,234 A | 6/2000 | Khokhar et al. |
| D313,067 S | 12/1990 | Kotake et al. | | 6,077,259 A | 6/2000 | Caizza et al. |
| D313,277 S | 12/1990 | Haining | | 6,082,401 A | 7/2000 | Braun et al. |
| D314,050 S | 1/1991 | Sone | | 6,135,150 A | 10/2000 | Powell et al. |
| 4,982,736 A | 1/1991 | Schneider | | 6,135,992 A | 10/2000 | Wang |
| 4,991,880 A | 2/1991 | Bernart | | 6,152,914 A | 11/2000 | Van De Kerkhof et al. |
| 5,009,252 A | 4/1991 | Faughn | | 6,161,578 A | 12/2000 | Braun et al. |
| 5,033,777 A | 7/1991 | Blenkush | | 6,182,694 B1 | 2/2001 | Sievers et al. |
| 5,052,725 A | 10/1991 | Meyer et al. | | 6,189,560 B1 | 2/2001 | Reynolds |
| 5,076,615 A | 12/1991 | Sampson | | 6,199,919 B1 | 3/2001 | Kawasaki et al. |
| 5,078,429 A | 1/1992 | Braut et al. | | 6,221,064 B1 | 4/2001 | Nadal |
| 5,090,448 A | 2/1992 | Truchet | | 6,231,089 B1 | 5/2001 | DeCler et al. |
| 5,090,747 A | 2/1992 | Kotake | | D444,054 S | 6/2001 | Bernard et al. |
| 5,104,158 A | 4/1992 | Meyer et al. | | 6,261,282 B1 | 7/2001 | Jepson et al. |
| D326,155 S | 5/1992 | Boehringer et al. | | 6,293,596 B1 | 9/2001 | Kinder |
| 5,114,250 A | 5/1992 | Usui | | 6,302,147 B1 | 10/2001 | Rose et al. |
| 5,165,733 A | 11/1992 | Sampson | | 6,318,764 B1 | 11/2001 | Trede et al. |
| D333,178 S | 2/1993 | Novy | | 6,344,033 B1 | 2/2002 | Jepson et al. |
| 5,190,224 A | 3/1993 | Hamilton | | D459,206 S | 6/2002 | Caveney et al. |
| 5,222,279 A | 6/1993 | Frano et al. | | 6,402,207 B1 | 6/2002 | Segal et al. |
| 5,228,724 A | 7/1993 | Godeau | | 6,423,053 B1 | 7/2002 | Lee |
| 5,232,020 A | 8/1993 | Mason et al. | | 6,481,759 B1 | 11/2002 | Kawasaki et al. |
| D339,417 S | 9/1993 | Sampson et al. | | 6,485,483 B1 | 11/2002 | Fujii |
| 5,316,041 A | 5/1994 | Ramacier, Jr. et al. | | 6,505,866 B1 | 1/2003 | Nakamura et al. |
| 5,356,183 A | 10/1994 | Cole | | 6,540,263 B1 | 4/2003 | Sausner |
| 5,374,088 A | 12/1994 | Moretti et al. | | 6,595,964 B2 | 7/2003 | Finley et al. |
| 5,385,311 A | 1/1995 | Morikawa et al. | | 6,612,634 B1 | 9/2003 | Zoppas |
| 5,385,331 A | 1/1995 | Allread et al. | | 6,626,465 B2 | 9/2003 | Lacroix et al. |
| 5,405,339 A | 4/1995 | Kohnen et al. | | 6,641,177 B1 | 11/2003 | Pinciaro |
| 5,405,340 A | 4/1995 | Fageol et al. | | 6,652,007 B1 | 11/2003 | Hwang |
| 5,437,650 A | 8/1995 | Larkin et al. | | 6,669,681 B2 | 12/2003 | Jepson et al. |
| 5,494,074 A | 2/1996 | Ramacier, Jr. et al. | | 6,676,172 B2 | 1/2004 | Alksnis |
| 5,507,733 A | 4/1996 | Larkin et al. | | 6,722,705 B2 | 4/2004 | Korkor |
| D372,093 S | 7/1996 | Sampson et al. | | 6,783,520 B1 | 8/2004 | Candray et al. |
| 5,536,258 A | 7/1996 | Folden | | 6,799,747 B1 | 10/2004 | Lai |
| 5,547,166 A | 8/1996 | Engdahl | | 6,840,277 B1 | 1/2005 | Nimberger |
| 5,553,895 A | 9/1996 | Karl et al. | | 6,871,878 B2 * | 3/2005 | Miros ...................... 285/124.5 |
| D375,160 S | 10/1996 | Sampson et al. | | D503,778 S | 4/2005 | Wicks |
| 5,568,946 A | 10/1996 | Jackowski | | 6,949,084 B2 | 9/2005 | Marggi et al. |
| 5,595,217 A | 1/1997 | Gillen et al. | | 6,997,919 B2 | 2/2006 | Olsen et al. |
| 5,628,726 A | 5/1997 | Cotter | | 7,005,581 B2 | 2/2006 | Burnette |
| D388,876 S | 1/1998 | Sampson | | 7,128,348 B2 | 10/2006 | Kawamura et al. |
| 5,709,244 A | 1/1998 | Patriquin et al. | | 7,137,654 B2 | 11/2006 | Segal et al. |
| 5,737,810 A | 4/1998 | Krauss | | 7,147,252 B2 | 12/2006 | Teuscher et al. |
| 5,745,957 A | 5/1998 | Khokhar et al. | | 2001/0054819 A1 | 12/2001 | Guest |
| 5,746,414 A | 5/1998 | Weldon et al. | | 2003/0193188 A1 * | 10/2003 | Miros ...................... 285/124.5 |
| 5,799,987 A | 9/1998 | Sampson | | 2005/0012330 A1 | 1/2005 | Schmidt |
| 5,845,943 A | 12/1998 | Ramacier, Jr. et al. | | 2005/0057042 A1 | 3/2005 | Wicks |
| 5,855,568 A | 1/1999 | Battiato et al. | | 2005/0082828 A1 | 4/2005 | Wicks et al. |
| 5,882,047 A | 3/1999 | Ostrander et al. | | 2007/0169825 A1 | 7/2007 | Packham et al. |
| D407,803 S | 4/1999 | Redman | | | | |
| 5,897,142 A | 4/1999 | Kulevsky | | * cited by examiner | | |

# FEMALE CONNECTOR FOR RELEASABLE COUPLING WITH A MALE CONNECTOR DEFINING A FLUID CONDUIT

FIELD OF THE INVENTION

The present invention relates to connectors for fluid conduits and methods of using such connectors. More particularly, the present invention relates to female connectors for releasable coupling with male connectors defining a fluid conduit and methods of manufacturing and using such connectors.

BACKGROUND OF THE INVENTION

Quick connect/disconnect coupling assemblies for small flexible tube applications and other applications are known in the art. Such couplings are utilized for biomedical applications, convenience handling, beverage dispensing, instrument connections, photochemical handling, etc. Despite the existence of such couplings, there is a need in the art for a female and male coupling arrangement that offers improved coupling security, simplified operation, and decreased manufacturing costs.

SUMMARY OF THE INVENTION

The present invention, in one embodiment, is a female connector for releasable coupling with a male connector. The male connector defines a first fluid conduit and includes a male end adapted to be received within the female connector. The male end includes a coupling feature. The female connector comprises a second fluid conduit, an opening, and a collet finger. The opening is adapted to receive the male end such that the first and second fluid conduits are placed in fluid communication when the male end is fully inserted into the opening. The collet finger includes an engagement feature adapted to engage the coupling feature of the male end and displace generally laterally to a travel direction of the male end when the male end is being inserted into the opening.

In one embodiment, the opening of the female connector is defined by a collar having a window through which the engagement feature displaces when the male end is inserted into the opening.

In one embodiment, the engagement feature of the female connector includes an arcuate leading edge, an arcuate lip adapted to engage the coupling feature of the male end, and an arcuate beveled surface located between the arcuate leading edge and the arcuate lip. In one embodiment, the arcuate leading edge is defined by a first radius and the arcuate lip is defined by a second radius that is smaller than the first radius. In one embodiment, the engagement feature further includes a first arcuate wall portion extending from the arcuate leading edge to the arcuate beveled surface. In one embodiment, the engagement feature further includes a second arcuate wall portion extending from the arcuate beveled surface to the arcuate lip. In one embodiment, the coupling feature of the male end is a groove and the first arcuate wall portion resides within the groove when the engagement feature engages the coupling feature.

In one embodiment, the female connector further includes a biasing element adapted to bring the engagement feature into contact with the coupling feature of the male end. In one embodiment, the collet finger of the female connector includes an integral biasing element adapted to bring the engagement feature into contact with the coupling feature of the male end.

In one embodiment, the female connector further comprises a button including a member extending therefrom adapted to cause the engagement feature to displace laterally away from the coupling feature upon depressing the button. In one embodiment, the member is a wedge that is adapted to engage an inclined surface of the collet finger. In one embodiment, the member moves generally laterally to the displacement direction of the collet finger and the travel direction of the male end.

In one embodiment, the female connector further comprises a housing generally containing the collet finger and supporting the button. In one embodiment, the button is pivotally coupled to the housing.

In one embodiment, the female connector further comprises a biasing element extending between the housing and the button to bias the member away from the collet finger. In one embodiment, the button includes a latch extending therefrom adapted to engage the housing to prevent the button from overly biasing away from the collet finger.

The present invention, in one embodiment, is a female connector for releasable coupling with a male connector. The male connector defines a first fluid conduit and includes a male end adapted to be received within the female connector. The male end includes a coupling feature. The female connector comprises an opening, a collet finger, and an actuation element. The opening is adapted to guide the male connector along a first line of action as the male connector passes into the opening to be received within the female connector. The collet finger includes an engagement feature adapted to engage the coupling feature of the male end and displace along a second line of action generally normal to the first line of action. The actuation element is adapted to displace along a third line of action generally normal to the first and second lines of action in order to disengage the engagement feature from the coupling feature of the male end.

In one embodiment, the female connector further comprises a button from which the actuation element extends. In one embodiment, the female connector further comprises a housing and the button is pivotally coupled to the housing. In one embodiment, the substantially encloses the collet finger and supports the button.

In one embodiment, the female connector further includes first and second biasing elements. The first biasing element acts against the collet finger to bias the engagement feature into engagement with the coupling feature of the male end. The second biasing element acts against the button to bias the actuation element away from the collet finger.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION OF THE INVENTION

Figure 1A:
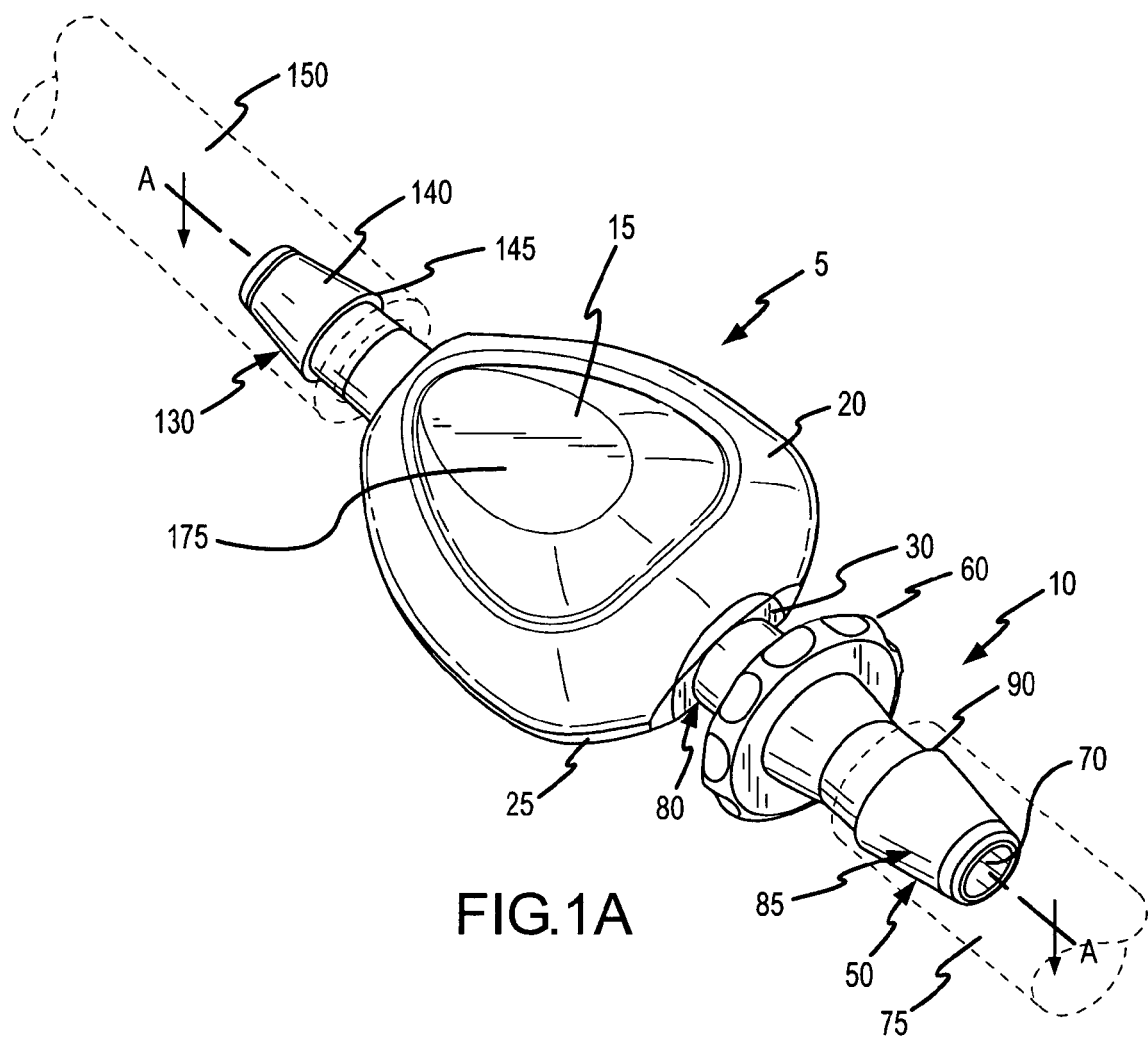
FIG. 1A is a top-front isometric view of a female quick-connect coupler of the subject invention coupled to a male connector.

FIG. 1A is a top-front isometric view of a female quick-connect coupler 5 of the subject invention coupled to a male connector 10. As will be understood from the following discussion, in one embodiment, the female coupler 5 includes an engagement feature and the male connector 10 includes a coupling feature. The engagement feature is housed within the housing 12 of the female coupler 5 and is adapted to positively engage with the coupling feature of the male connector 10. Upon insertion of the male connector 10 into the female coupler 5, the male connector 10 positively couples with the female coupler 5. Depressing an actuation button 15 on the female coupler 5 disengages the engagement feature from the coupling feature, thereby allowing the male connector 10 to be withdrawn from the female coupler 5.

Figure 1B:
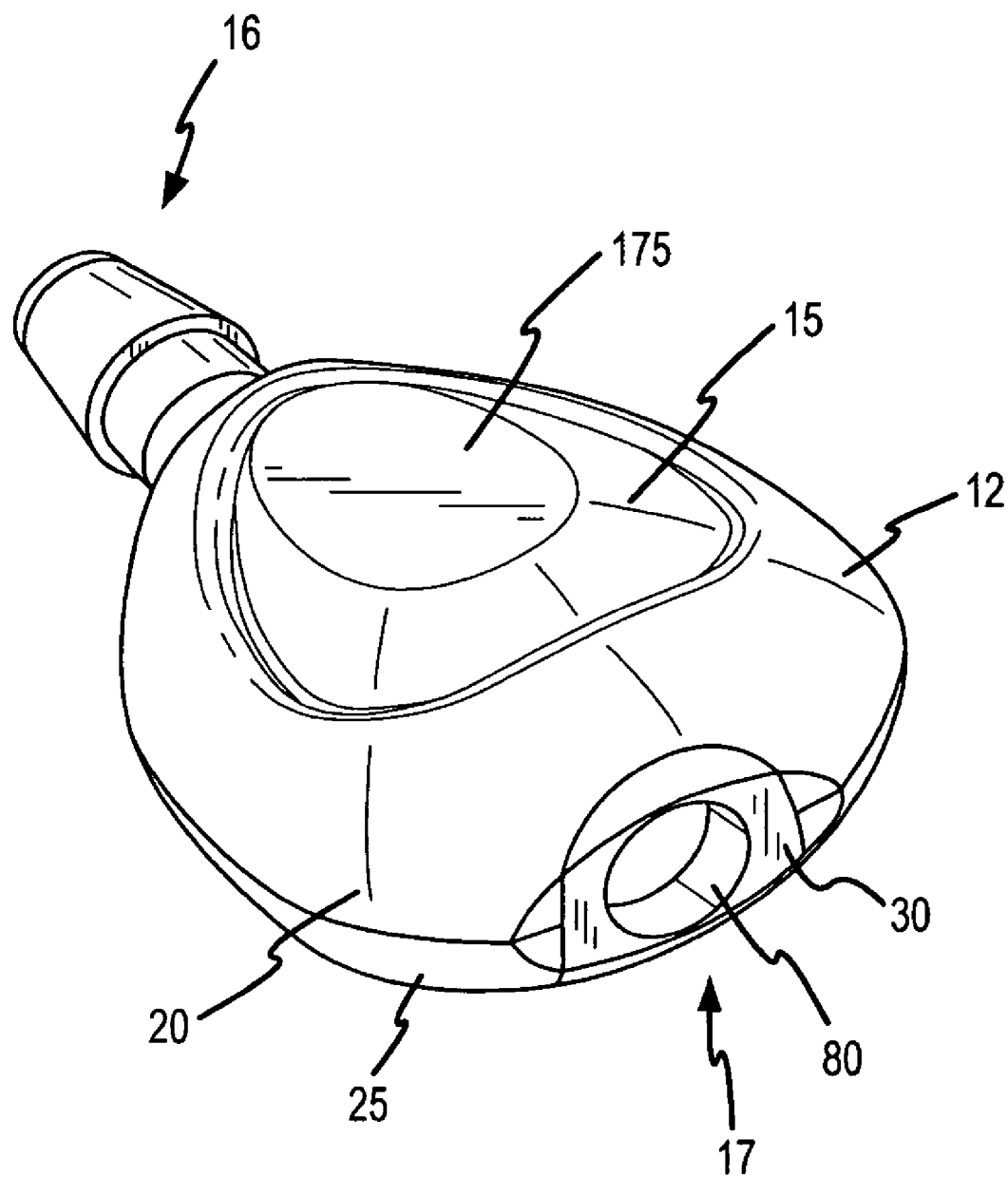
FIG. 1B is a top-front isometric view of the female coupler.
Figure 1C:
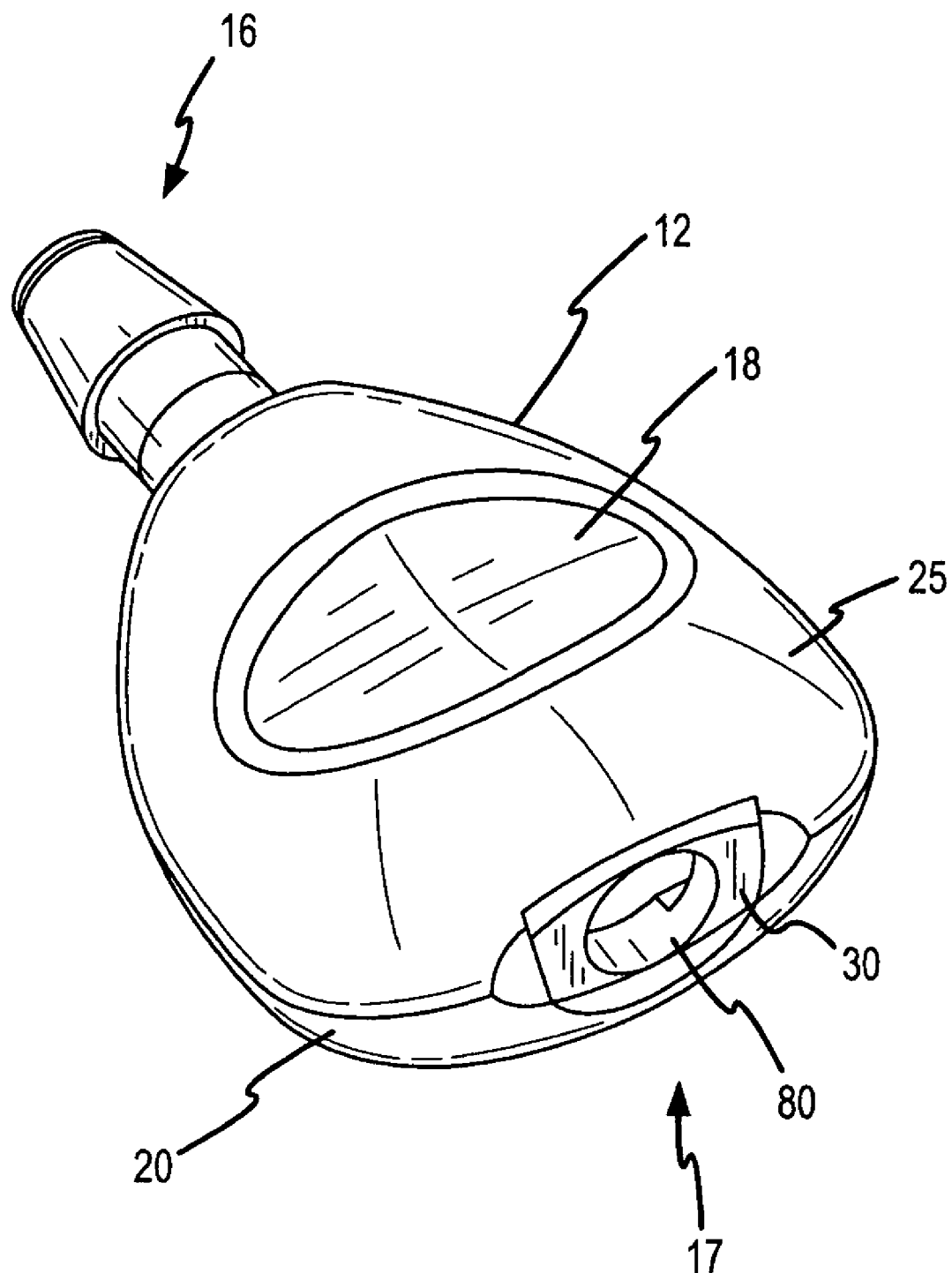
FIG. 1C is a bottom-front isometric view of the female coupler.
Figure 1D:
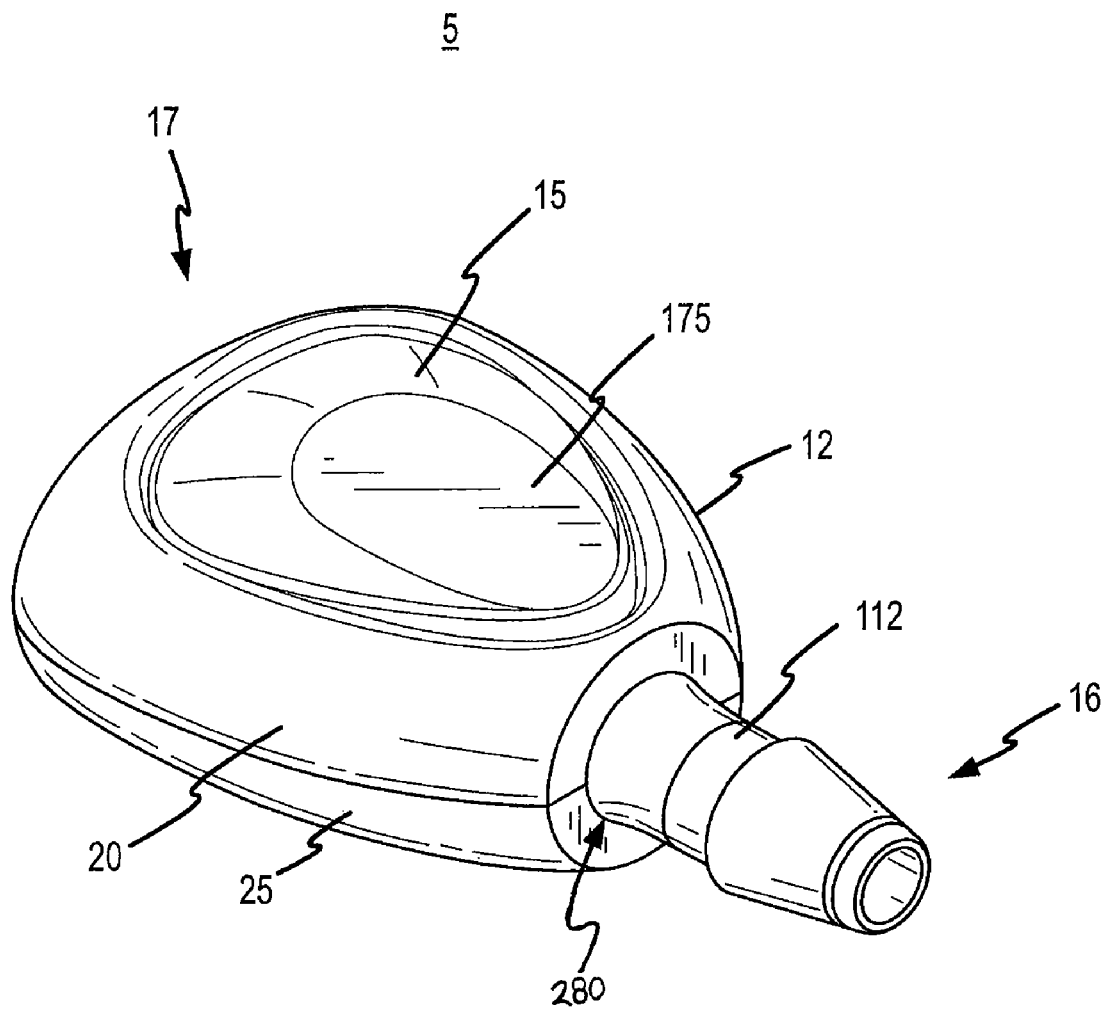
FIG. 1D is a top-rear isometric view of the female coupler.
Figure 1E:
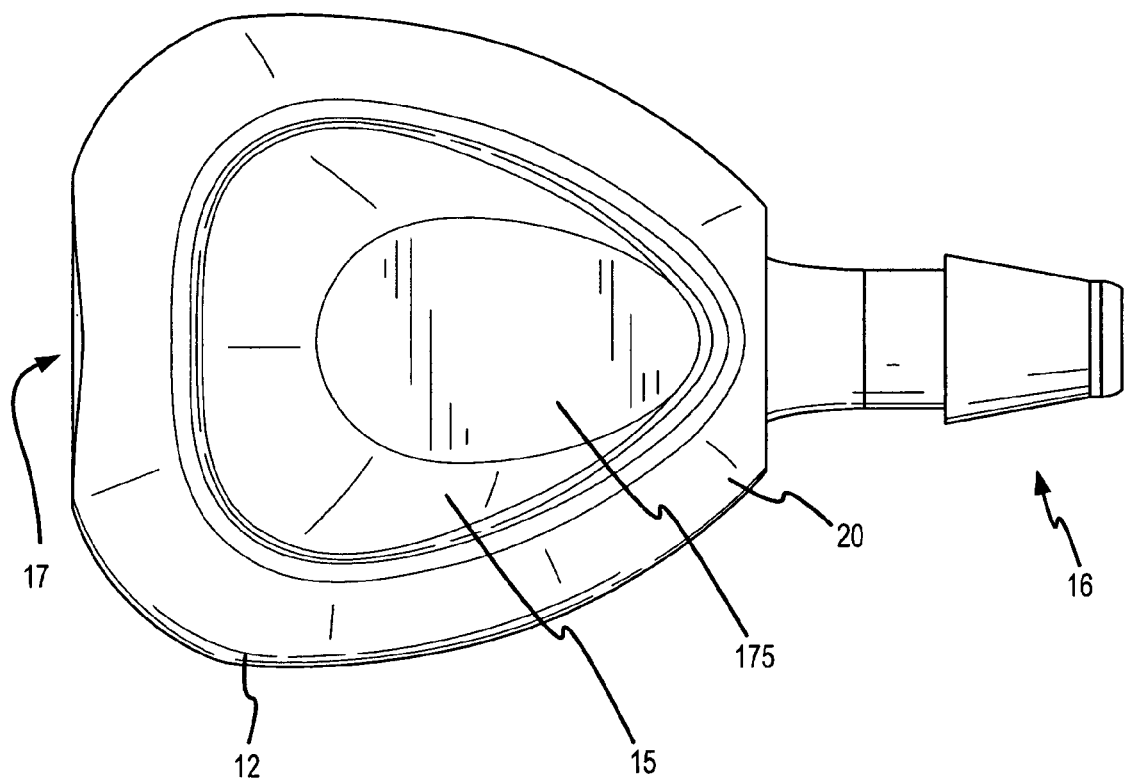
FIG. 1E is a top plan view of the female coupler.
Figure 1F:
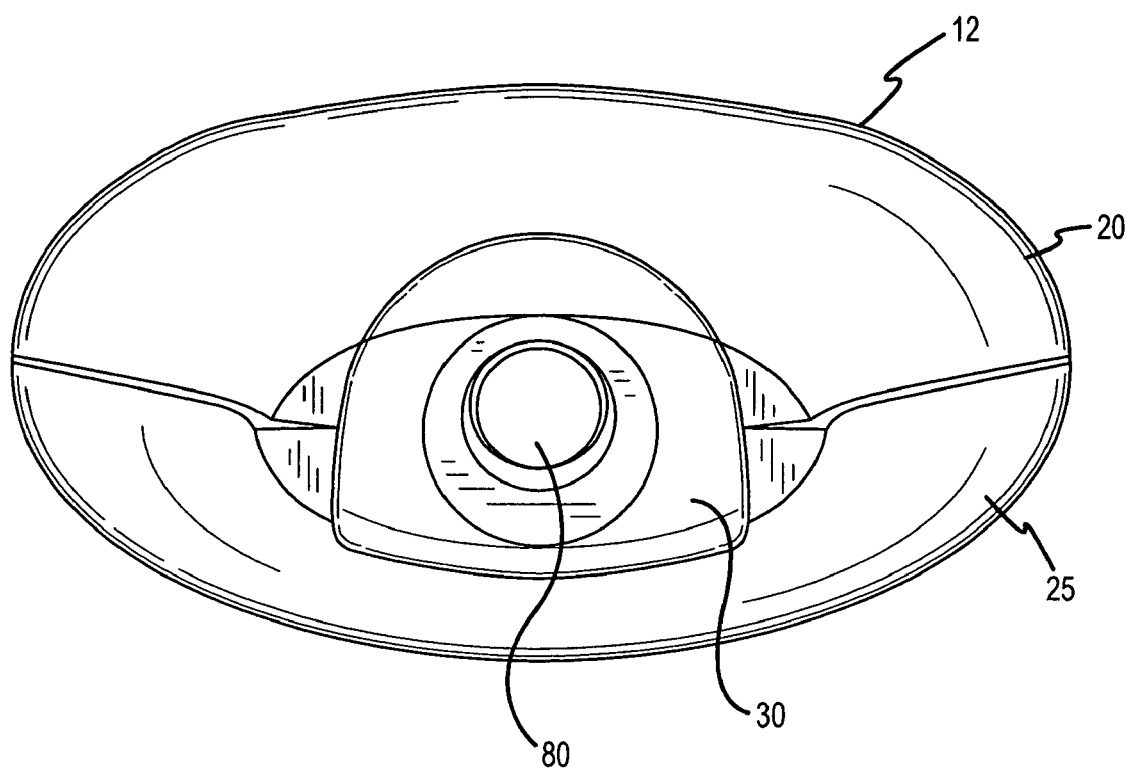
FIG. 1F is a front elevation of the female coupler.
Figure 1G:
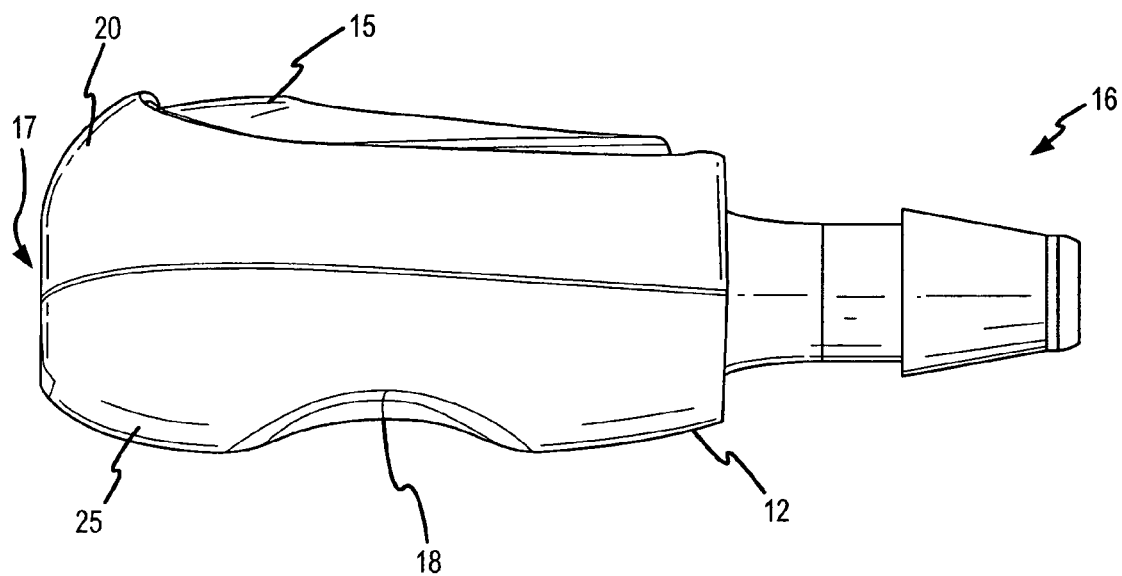
FIG. 1G is a right side elevation of the female coupler.
Figure 1H:
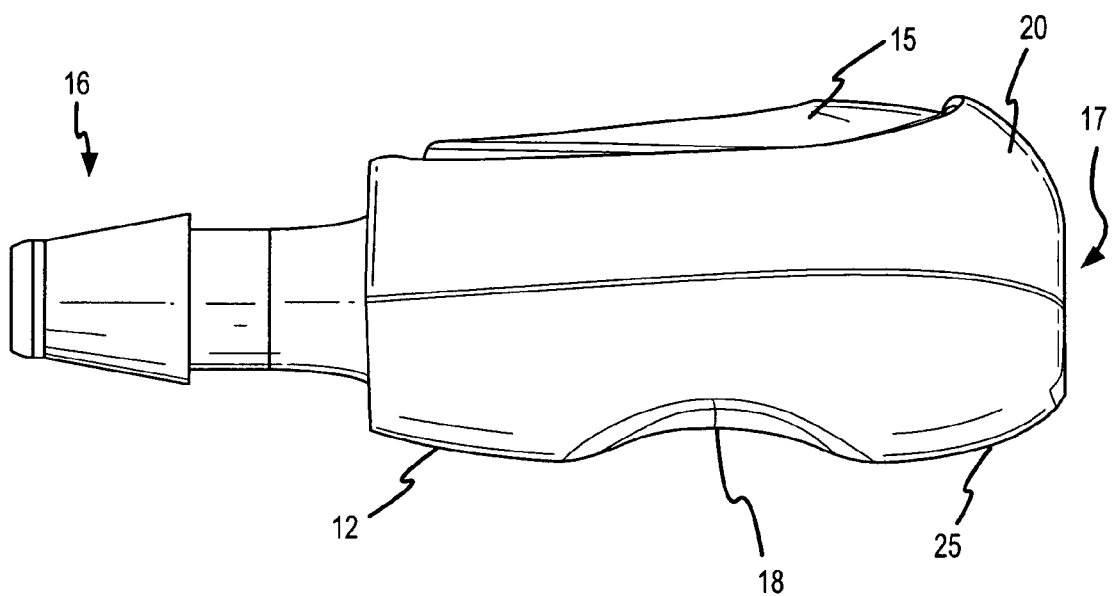
FIG. 1H is a left side elevation of the female coupler.
Figure 1I:
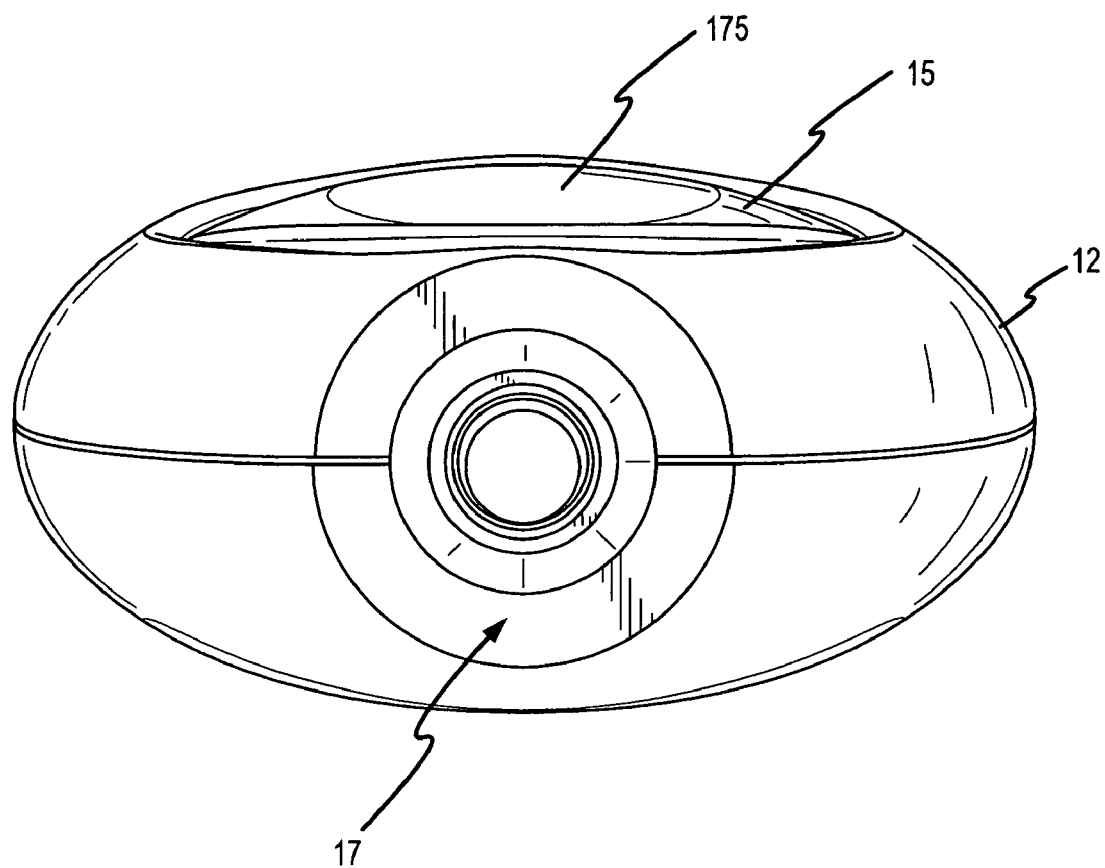
FIG. 1I is a rear elevation of the female coupler.
Figure 1J:
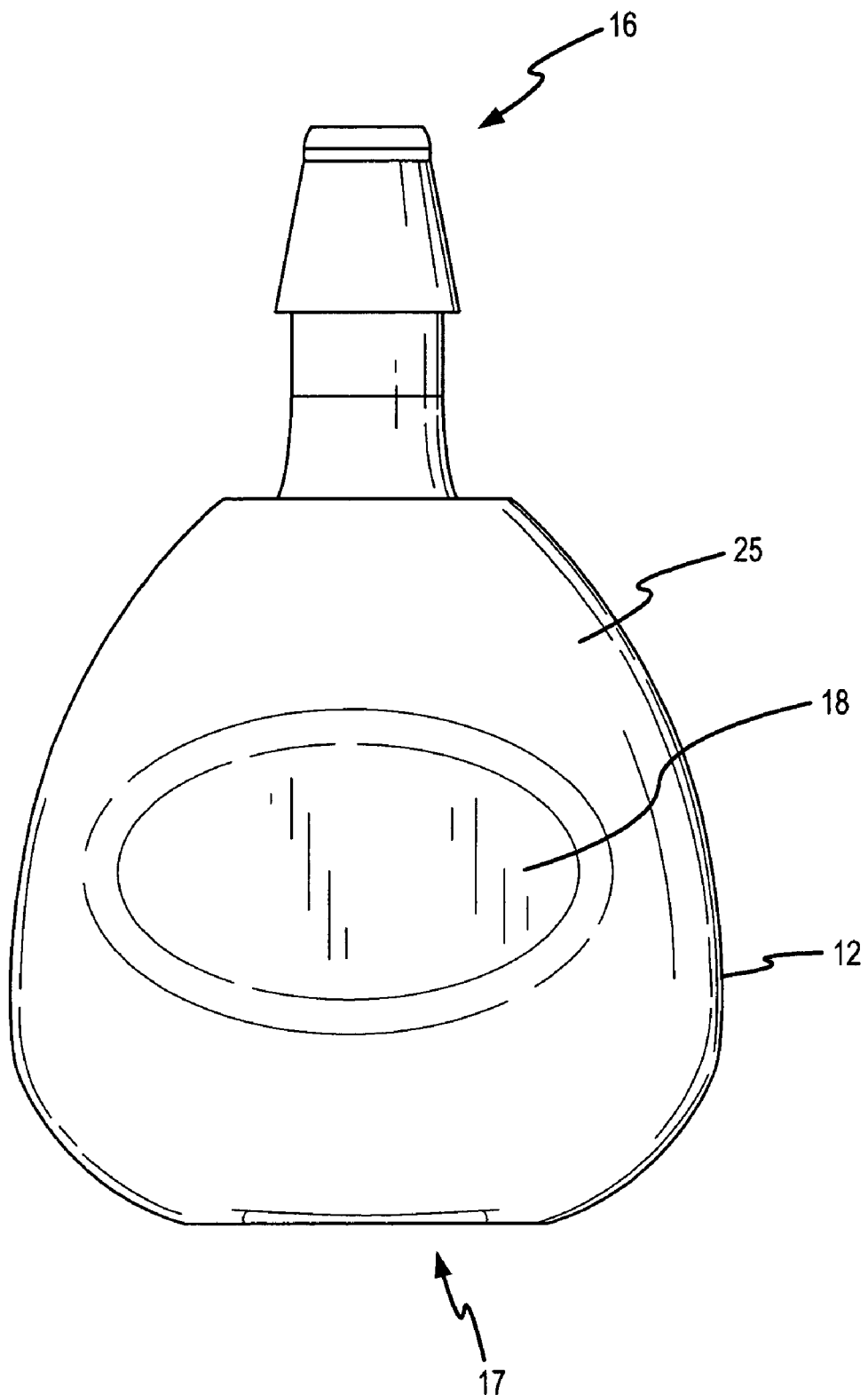
FIG. 1J is a bottom plan view of the female coupler.

For a discussion of the overall configuration of the female quick-connect coupler 5 of the subject invention, reference is now made to FIGS. 1B-1J. FIG. 1B is a top-front isometric view of the female coupler 5. FIG. 1C is a bottom-front isometric view of the female coupler 5. FIG. 1D is a top-rear isometric view of the female coupler 5. FIG. 1E is a top plan view of the female coupler 5. FIG. 1F is a front elevation of the female coupler 5. FIG. 1G is a right side elevation of the female coupler 5. FIG. 1H is a left side elevation of the female coupler 5. FIG. 1I is a rear elevation of the female coupler 5. FIG. 1J is a bottom plan view of the female coupler 5.

As shown in FIGS. 1B-1J, the female coupler 5 includes a male end 16, a female end 17, and an actuation button 15. As illustrated in FIG. 1A, the female end 17 is configured to be connected to a first fluid conduit by receiving the first conduit within the female end 17, and the male end 16 is configured to be connected to a second fluid conduit by being received within the second conduit.

As can be understood from FIGS. 1B-1J, the female coupler 5 has a generally almond-shaped rounded housing 12 that gracefully curves from surface to surface. As a result, the female coupler 5 and its housing 12 are both ergonomic and attractive. As shown in FIGS. 1B, 1D, 1E and 1I, the button includes a generally oval-shaped recess 175 for receiving a user's thumb. The longitudinal axis of the oval-shaped recess 175 extends generally parallel to the longitudinal axis of the overall female coupler 5.

As indicated in FIGS. 1C, 1G, 1H and 1J, the bottom exterior surface of the housing 12 includes a second generally oval-shaped recess 18 for receiving a user's forefinger. The longitudinal axis of the second oval-shaped recess 18 extends generally perpendicular to the longitudinal axis of the overall female coupler 5. Due to the ergonomic configuration of the overall female coupler 5 and configuration and orientation of the two oval-shaped recesses 175, 18, the female coupler 5 can be comfortably held between a user's thumb and forefinger.

Figure 2:
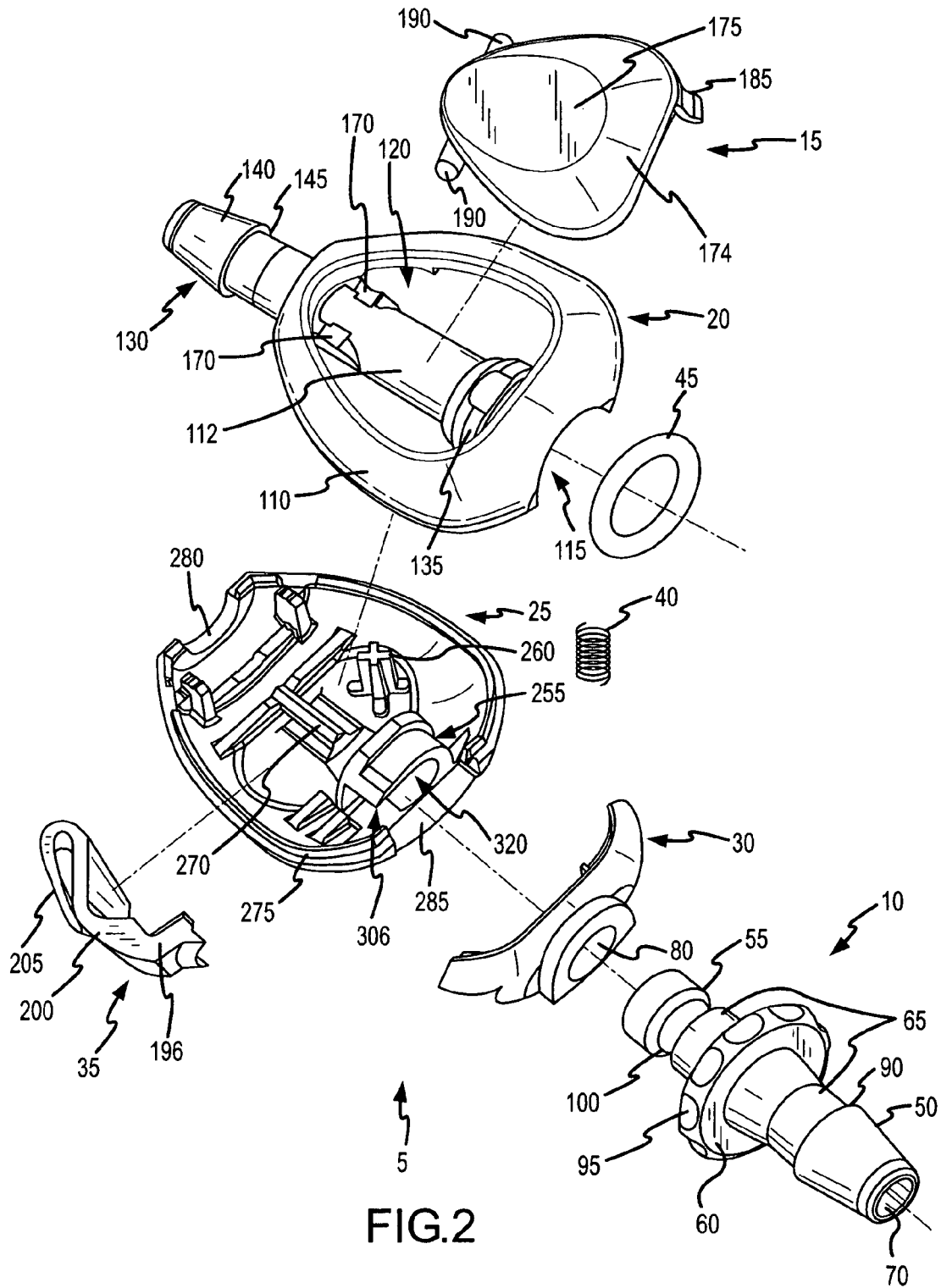
FIG. 2 is a top-front exploded isometric view of the female coupler and male connector.

For a discussion of the elements comprising the female coupler 5 of the subject invention, reference is now made to FIG. 2, which is an exploded top-front isometric view of the female coupler 5 and male connector 10. As shown in FIG. 2, the female coupler 5 includes the button 15, the housing 12 (which includes an upper housing portion 20, a lower housing portion 25, and a front housing portion 30), a collet finger 35, a helical spring 40, and an o-ring 45.

a. Male Connector

Figure 3:
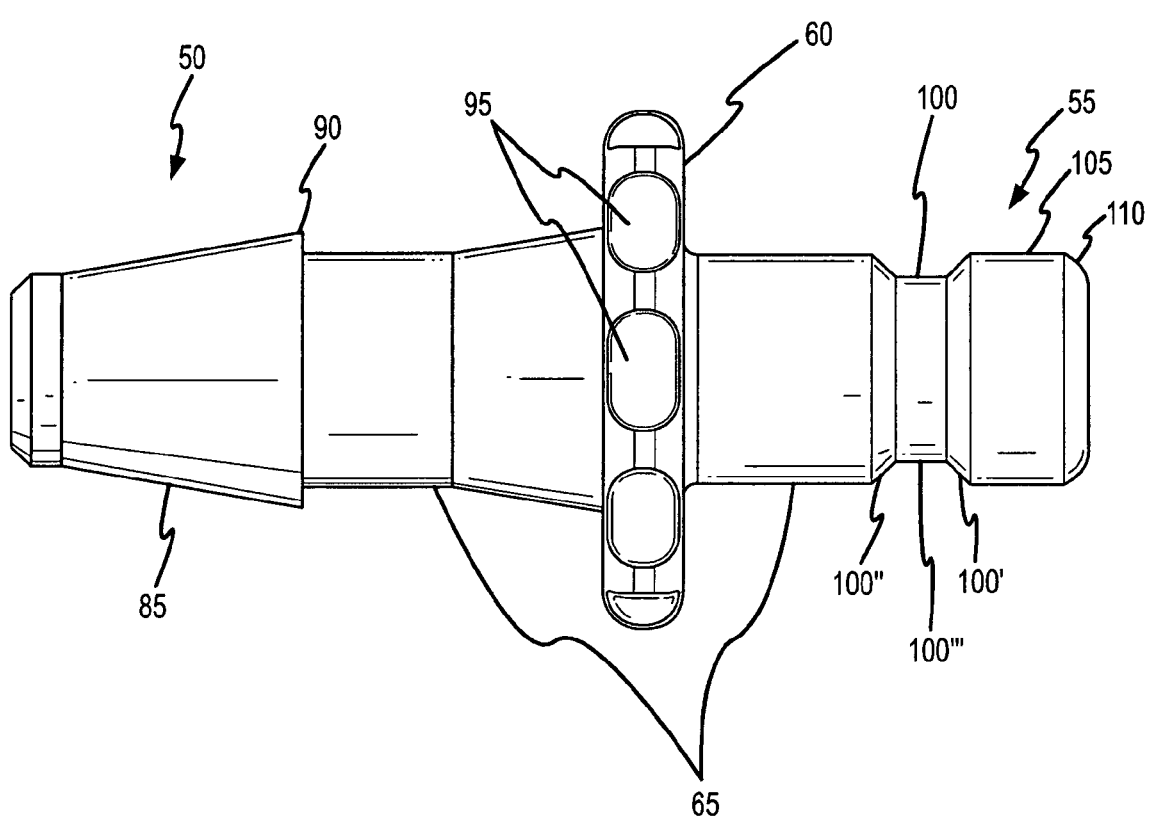
FIG. 3 is a side elevation of the male connector.

For a discussion of the features of the male connector 10, reference is now made to FIGS. 1A, 2 and 3. FIG. 3 is a side elevation of the male connector 10. As shown in FIGS. 2 and 3, the male connector 10 includes a barbed male end 50, a grooved male end 55, a disk portion 60, a longitudinally extending body 65, and a fluid conduit 70 extending through the male connector 10 from the grooved male end 55 to the barbed male end 50.

As can be understood from FIGS. 1A and 2, the barbed male end 50 is adapted to be received in a first tubular conduit 75 (illustrated in hidden lines), and the grooved male end 55 is received within an opening 80 defined in the front housing portion 30 of the female coupler 5. As shown in FIG. 3, the barbed male end 50 includes a tapered section 85 that increases in diameter as it extends from the tip of the barbed end 50 to a lip 90 that extends circumferentially about the body 65. The tapered section 85 facilitates the insertion of the barbed male end 50 into the first tubular conduit 75, and the lip 90 facilitates the retention of the barbed male end 50 in the first tubular conduit 75.

As can be understood from FIG. 1A, the disk portion 60 serves as a grasping feature that allows a user to grasp the male connector 10 for its insertion into, or its removal from, the female coupler 5. As illustrated in FIGS. 1A, 2 and 3, the disk portion 60 includes bumps/knurls 95 that increase frictional contact between the disk portion 60 and a user to allow the user to rotate the male connector 10 as it is being inserted into the first tubular conduit 75.

As indicated in FIGS. 2 and 3, the grooved male end 55 includes a groove 100 extending circumferentially about the body 65 of the male connector 10. The groove 100 includes a leading beveled edge 100', a trailing beveled edge 100", and a recessed cylindrical segment 100''' between the beveled edges 100', 100". The recessed cylindrical segment 100''' forms the bottom surface of the groove 100. The groove 100 is offset from the tip of the grooved male end 55, thereby forming a cylindrical rim 105 that extends between a beveled edge 110 of the tip and the leading beveled edge 100' of the groove 100. As discussed later in this Detailed Description, when the grooved male end 55 is received within the opening 80 defined in the front housing portion 30 of the female coupler 5, the groove 100 serves as a coupling feature for engagement by an engagement feature of the female coupler 5. Engagement of the coupling feature (i.e., groove 100) of the male connector 10 by the engagement feature of the female coupler 5 couples the male connector 10 to the female coupler 5.

In one embodiment, the male connector 10 is formed from acetal. In another embodiment, the male connector 10 is formed from nylon. In yet other embodiments, the male connector 10 is formed from other appropriate polymers.

b. Upper Housing Portion

Figure 4:
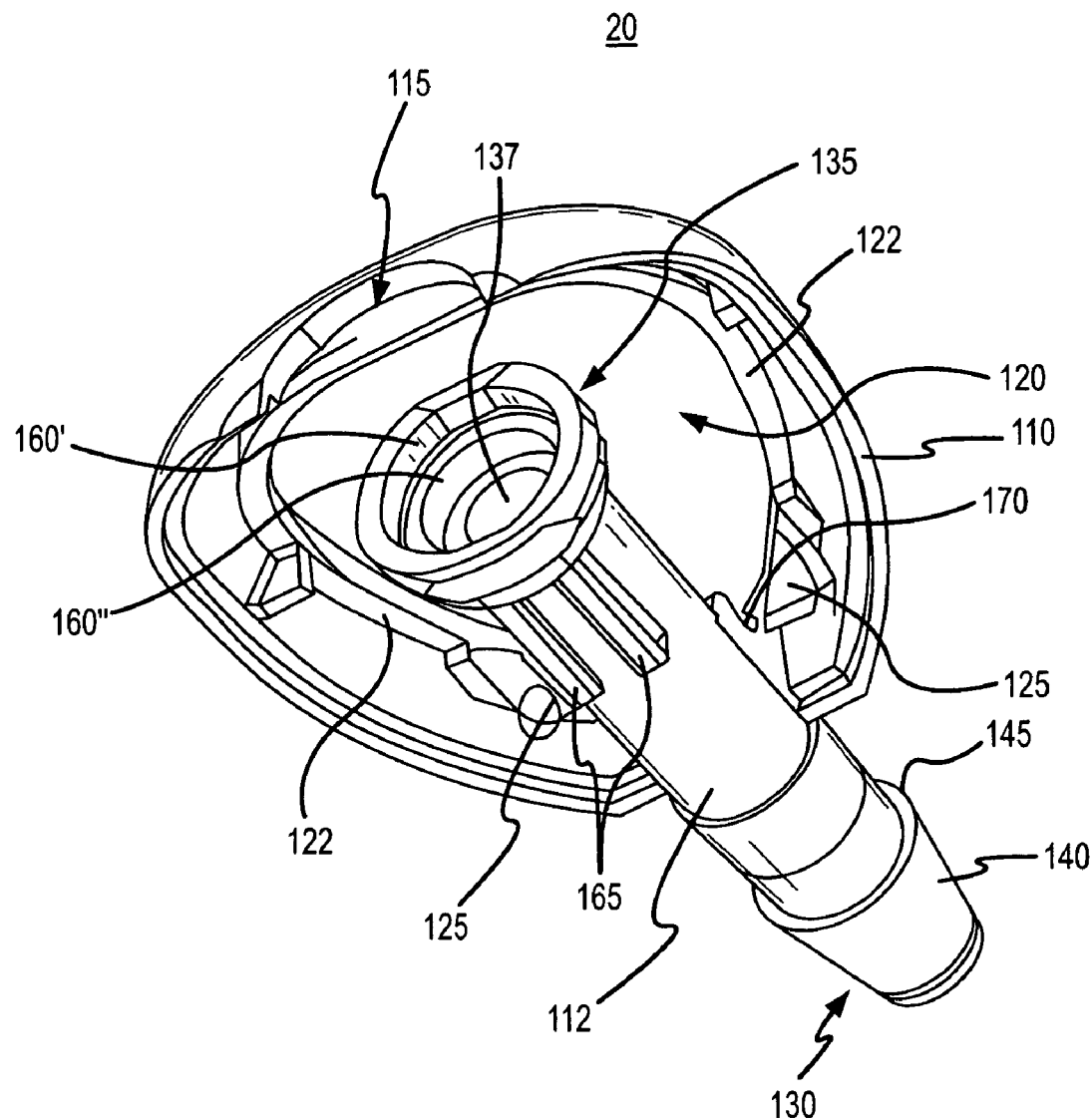
FIG. 4 is a bottom-front isometric view of the upper housing portion.
Figure 5:
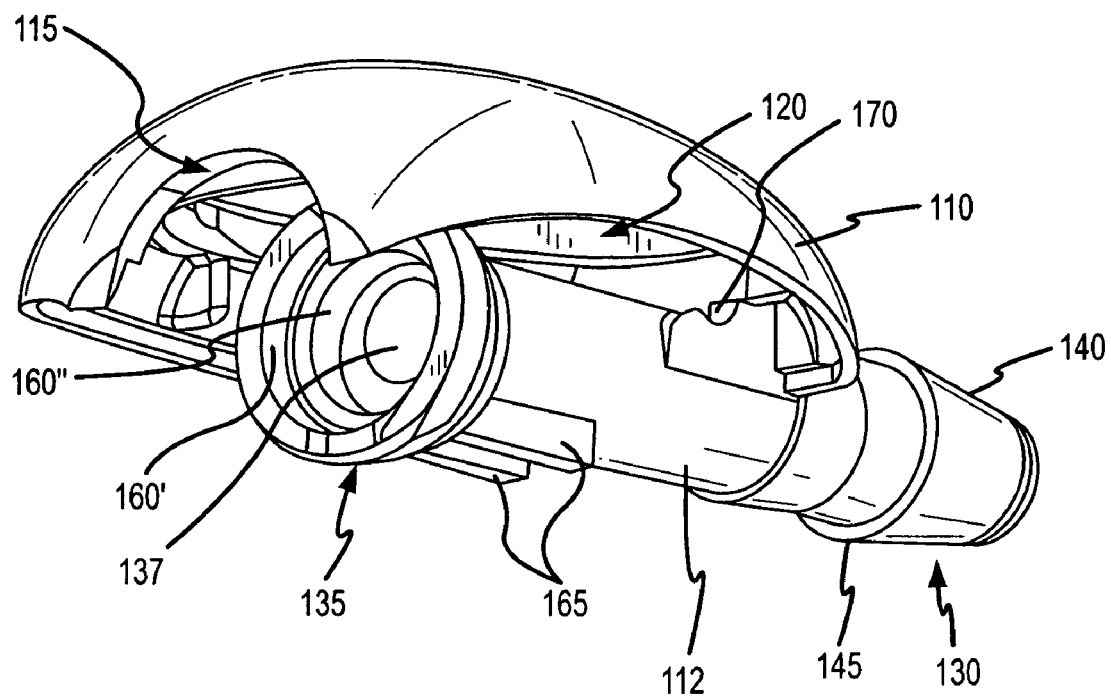
FIG. 5 is another bottom-front isometric view of the upper housing portion.
Figure 6:
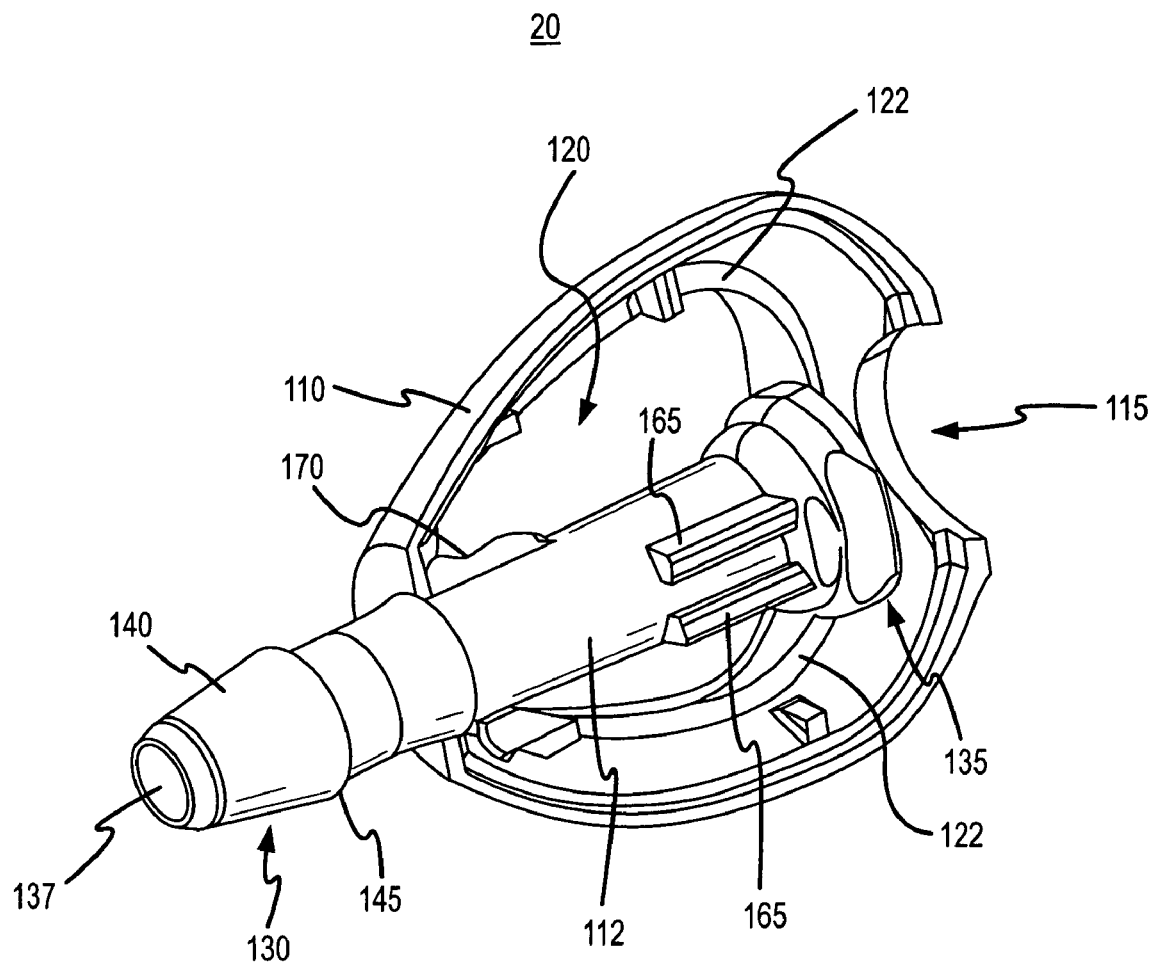
FIG. 6 is bottom-rear isometric view of the upper housing portion.

For a discussion of the features of the upper housing portion 20, reference is now made to FIGS. 1A, 2 and 4-6. FIG. 4 is a bottom-front isometric view of the upper housing portion 20. FIG. 5 is another bottom-front isometric view of the upper housing portion 20. FIG. 6 is bottom-rear isometric view of the upper housing portion 20. FIGS. 1A and 2 illustrate the outer features of the upper housing portion 20, and FIGS. 4-6 illustrate the inner features of the upper housing portion 20.

As shown in FIGS. 1A, 2 and 4-6, in one embodiment, the upper housing portion 20 includes a shell wall 110 and a longitudinally extending body 112. The shell wall 110 has a rounded ergonomically shaped outer surface and joins the body 112 at a rear end of the upper housing portion 20 to form one integral piece. The shell wall 110 includes a semi-circular opening 115 at the front end of the upper housing portion 20, a top opening 120 for receiving the button 15 (as illustrated in FIG. 1A), and a lip 122 extending along the edge of the top opening 120. As illustrated in FIG. 4, rounded grooves 125 are located in the inner surface of the shell wall 110 near the intersection between the body 112 and the shell wall 110 on either side of the body 112. The rounded grooves 125 serve as the upper half of pivot pin brackets for retaining the pivot pins of the button, as discussed later in this Detailed Description.

As indicated in FIGS. 2 and 4-6, the longitudinally extending body 112 includes a barbed male end 130, a female end 135, and a fluid conduit 137 extending through the body 112 from the female end 135 to the male end 130. The barbed male end 130 includes a tapered section 140 that increases in diameter as it extends from the tip of the barbed end 130 to a lip 145 that extends circumferentially about the body 112. The tapered section 140 facilitates the insertion of the barbed male end 130 into a second tubular conduit 150 (illustrated in hidden lines in FIG. 1A), and the lip 145 facilitates the retention of the barbed male end 130 in the second tubular conduit 150.

Figure 16:
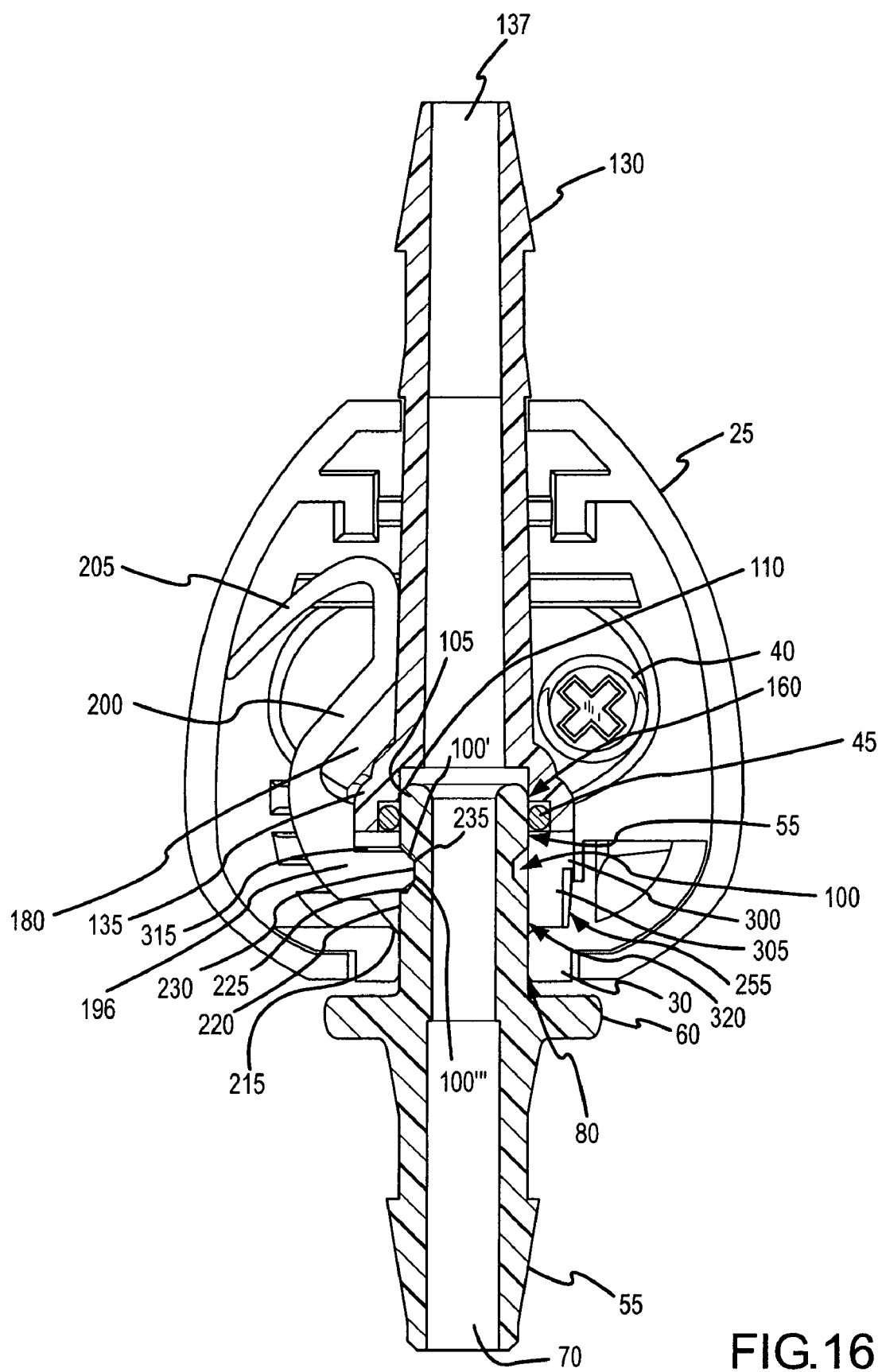
FIG. 16 is a horizontal cross section of the male connector coupled with the female coupler, as taken along section line AA in FIG. 1.

As illustrated in FIGS. 2, 4 and 5, the female end 135 is a bell-type socket with a stepped opening 160 (as shown in FIG. 16) defined by an outer section 160' and an inner section 160". The diameter of the outer section 160' exceeds the diameter of the inner section 160". The outer section 160' is sized to receive the o-ring 45 (FIG. 2) and the inner section 160" is sized to receive the grooved male end 55 of the male connector 10 when the male connector 10 is coupled with the female coupler 5, as shown in FIG. 1A.

As shown in FIGS. 2 and 4-6, the body 112 includes a pair of parallel ribs 165 extending longitudinally along the bottom surface of the body 112. The body 112 also includes a pair of curved saddles 170 that are located near the top surface of the body 112, near the intersection between the body 112 and the shell wall 110. The saddles 170 serve as the lower half of pivot pin brackets for retaining the pivot pins of the button, as will be discussed later in this Detailed Description.

In one embodiment, the upper housing portion 20 is formed from acrylonitrile-butadiene-styrene ("ABS"). In another embodiment, the upper housing portion 20 is formed from polycarbonate. In yet other embodiments, the upper housing portion 20 is formed from other appropriate polymers.

c. Button

Figure 7:
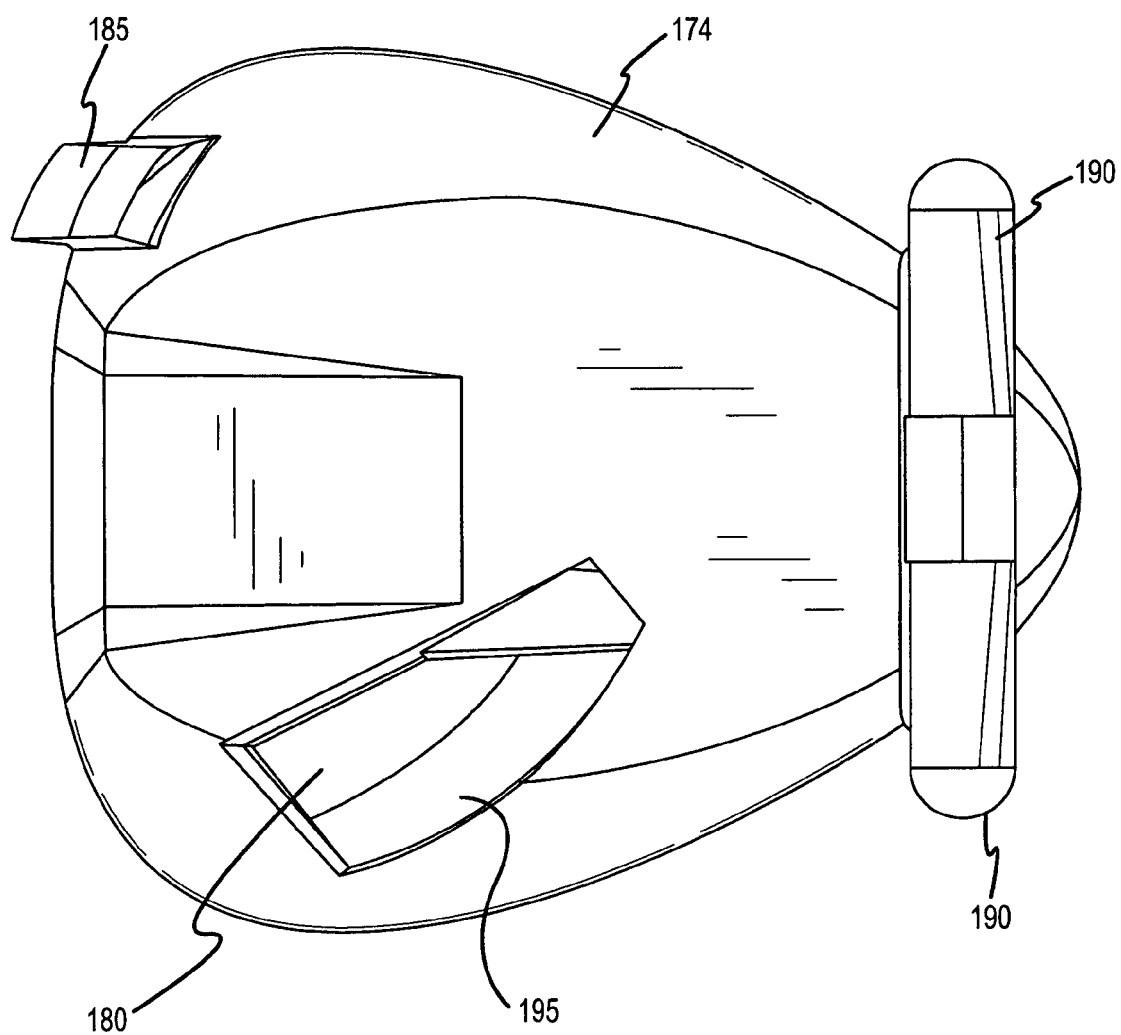
FIG. 7 is a bottom plan view of the button.
Figure 8:
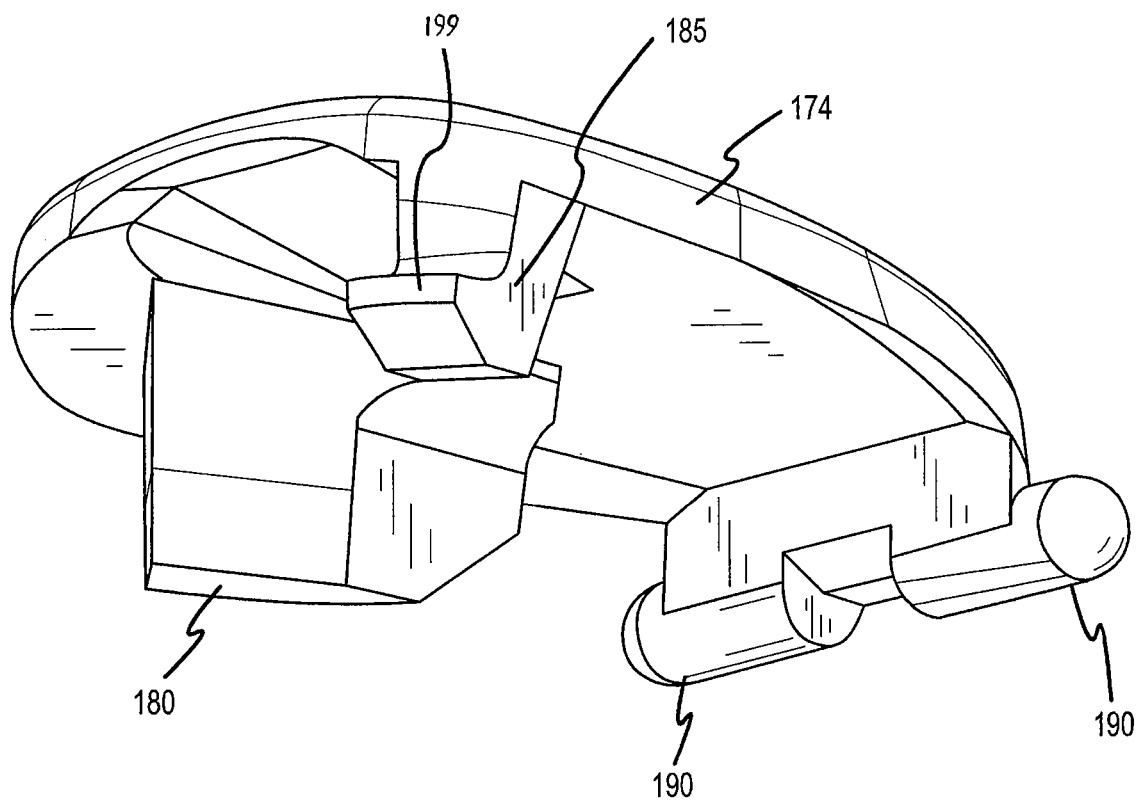
FIG. 8 is a bottom-front isometric view of the button.
Figure 9:
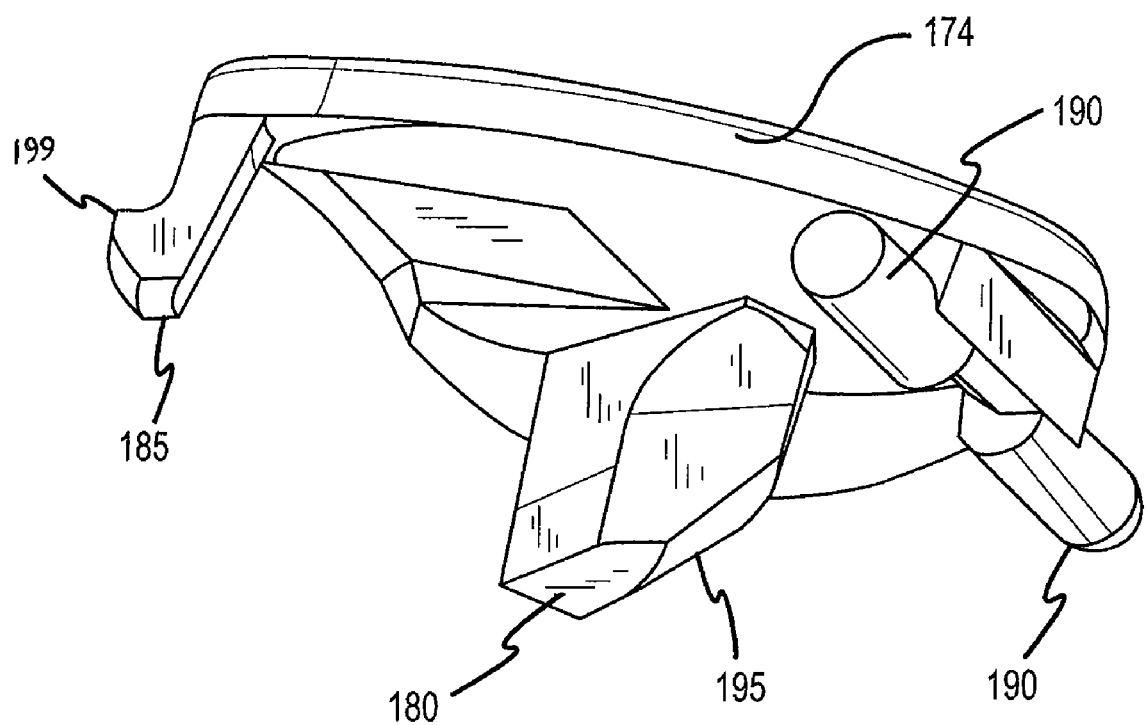
FIG. 9 is a bottom-rear isometric view of the button.
Figure 10:
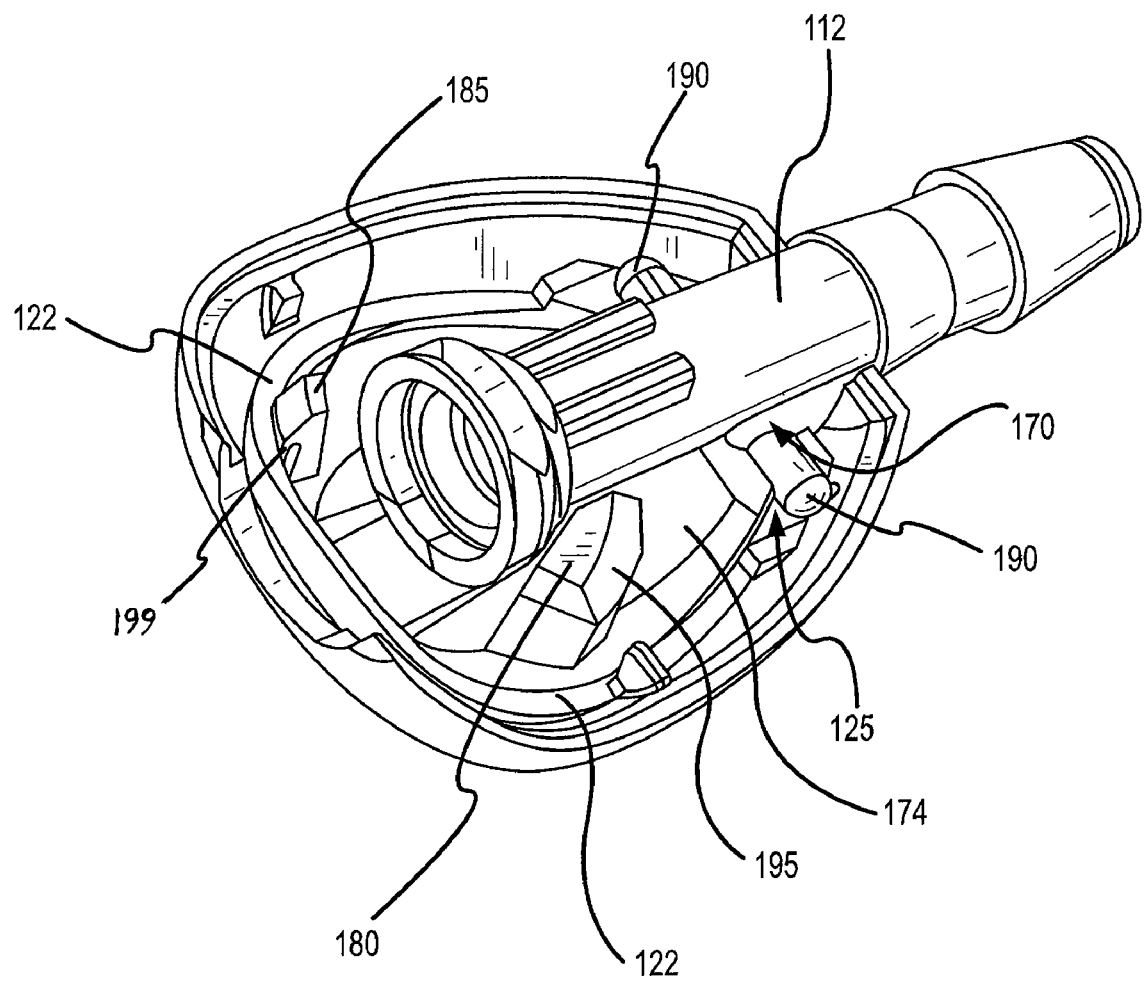
FIG. 10 is a bottom-front isometric view of the button pivotally coupled to the upper housing portion.

For a discussion of the features of the button 15, reference is now made to FIGS. 1A, 2 and 7-10. FIG. 7 is a bottom plan view of the button 15. FIG. 8 is a bottom-front isometric view of the button 15. FIG. 9 is a bottom-rear isometric view of the button 15. FIG. 10 is a bottom-front isometric view of the button 15 pivotally coupled to the upper housing portion 20. As shown in FIGS. 1A and 2, in one embodiment, the button 15 has a triangularly shaped platform 174 with an ergonomically shaped thumb receiving area 175 on the upper/outside surface of the platform 174.

As indicated in FIGS. 2 and 7-9, the button 15 includes a wedge member 180, a latch member 185, and a pair of pins 190. The wedge member 180 tapers as it extends downward from the bottom surface of the button platform 174. The wedge member 180 includes an arcuate inclined surface 195 for engaging a portion of the collet finger 35 to disengage the engagement feature of the collet finger 35 from the coupling feature of the male connector 10, as discussed later in this Detailed Description. The latch member 185 extends downward from the bottom surface of the button platform 174 and includes a lip 199 at the free end of the latch member 185. The pair of pins 190 extends downward from the bottom rear surface of the button platform 174, each pin extending generally perpendicularly away from the longitudinal centerline of the button platform 174.

As can be understood from FIG. 10, the lip 199 of the latch member 185 is configured to engage the lip 122 of the upper housing portion 20 to prevent the button 15 from overly biasing away from the rest of the female coupler 5 on account of the biasing force of the helical spring 40, as discussed later in this Detailed Description. Each pin 190 resides in a bracket formed by a rounded groove 125 and a curved saddle 170. This arrangement allows the button 15 to pivot about the pins 190 within the top opening 120 of the upper housing portion 20.

In one embodiment, the button 15 is formed from nylon. In another embodiment, the button 15 is formed from acetal. In yet other embodiments, the button 15 is formed from other appropriate polymers. In one embodiment, the helical spring 40 is formed from a metal such as 302 stainless steel.

d. Collet Finger

Figure 11:
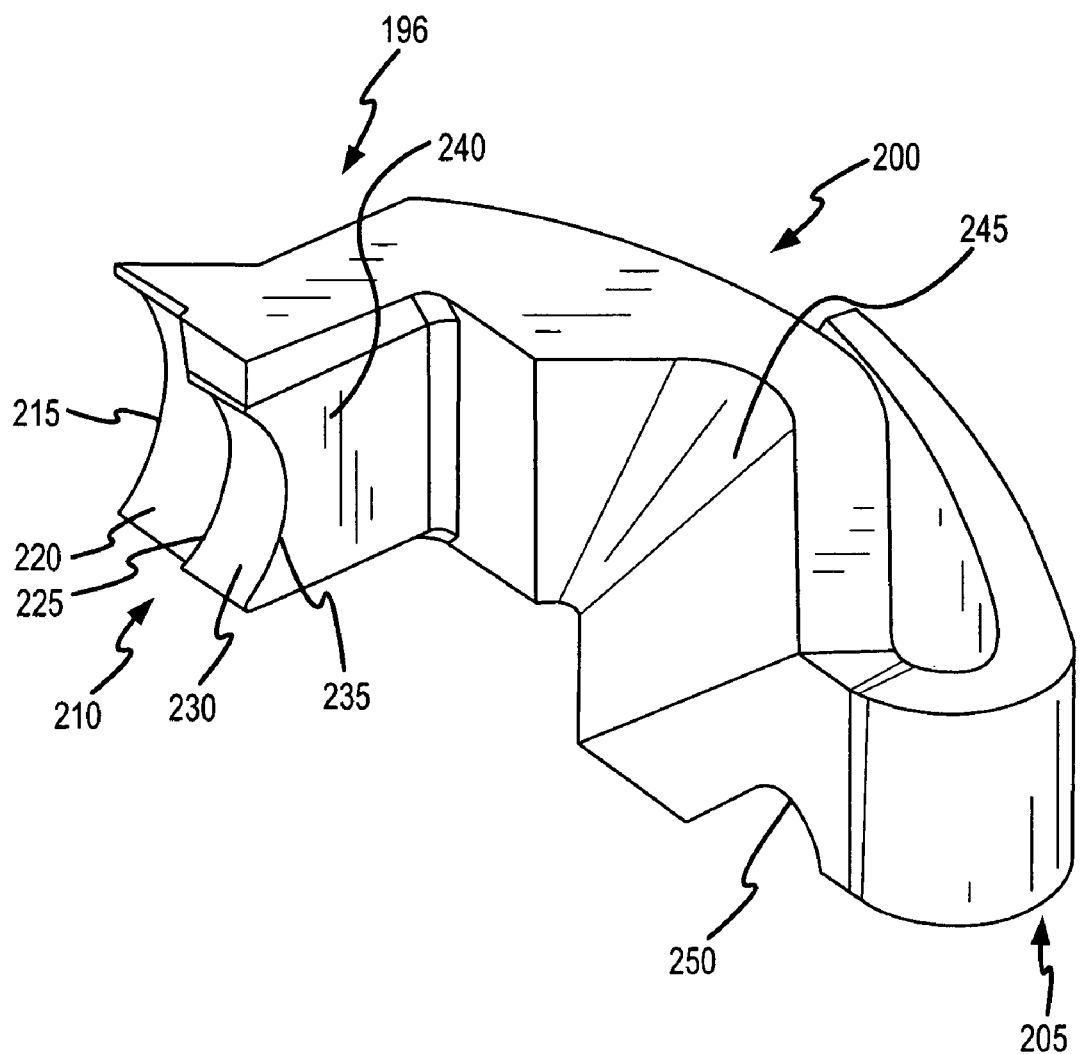
FIG. 11 is top-rear isometric view of the collet finger.
Figure 12:
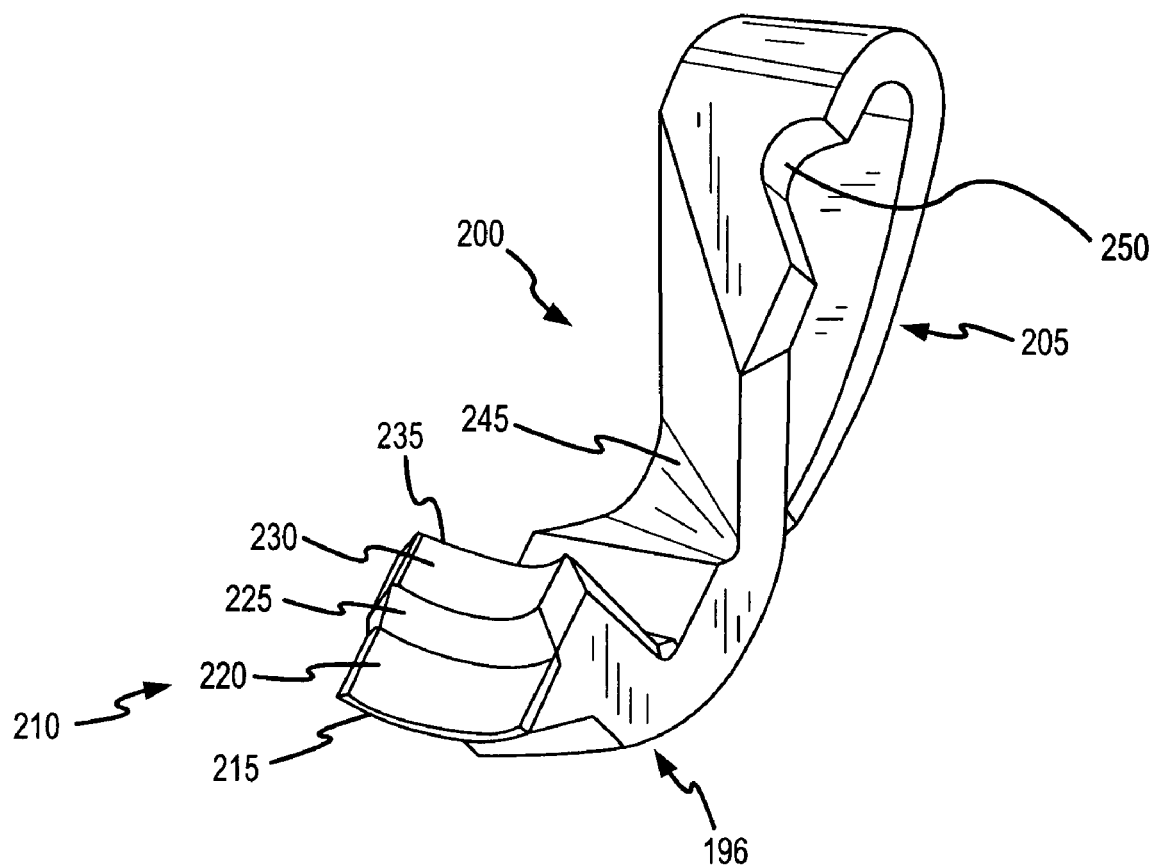
FIG. 12 is a bottom-front isometric view of the collet finger.
Figure 13:
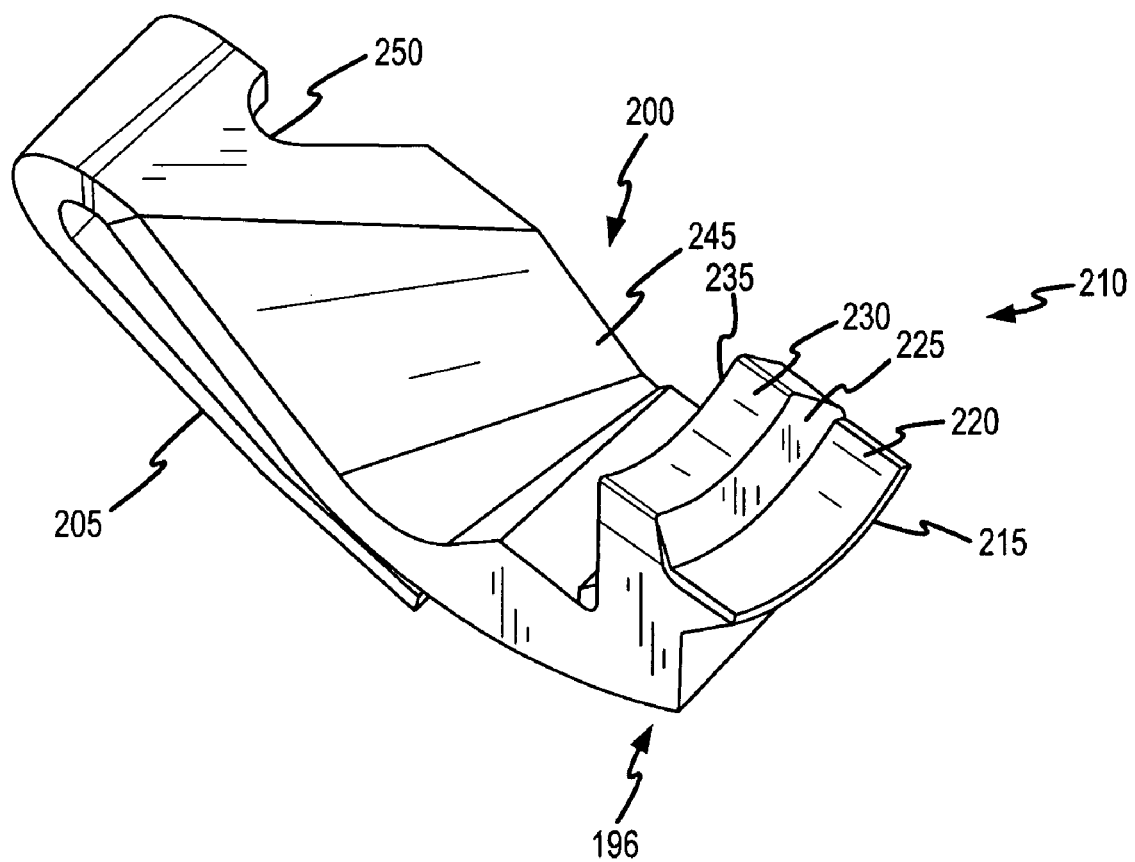
FIG. 13 is a top-front isometric view of the collet finger.
Figure 14:
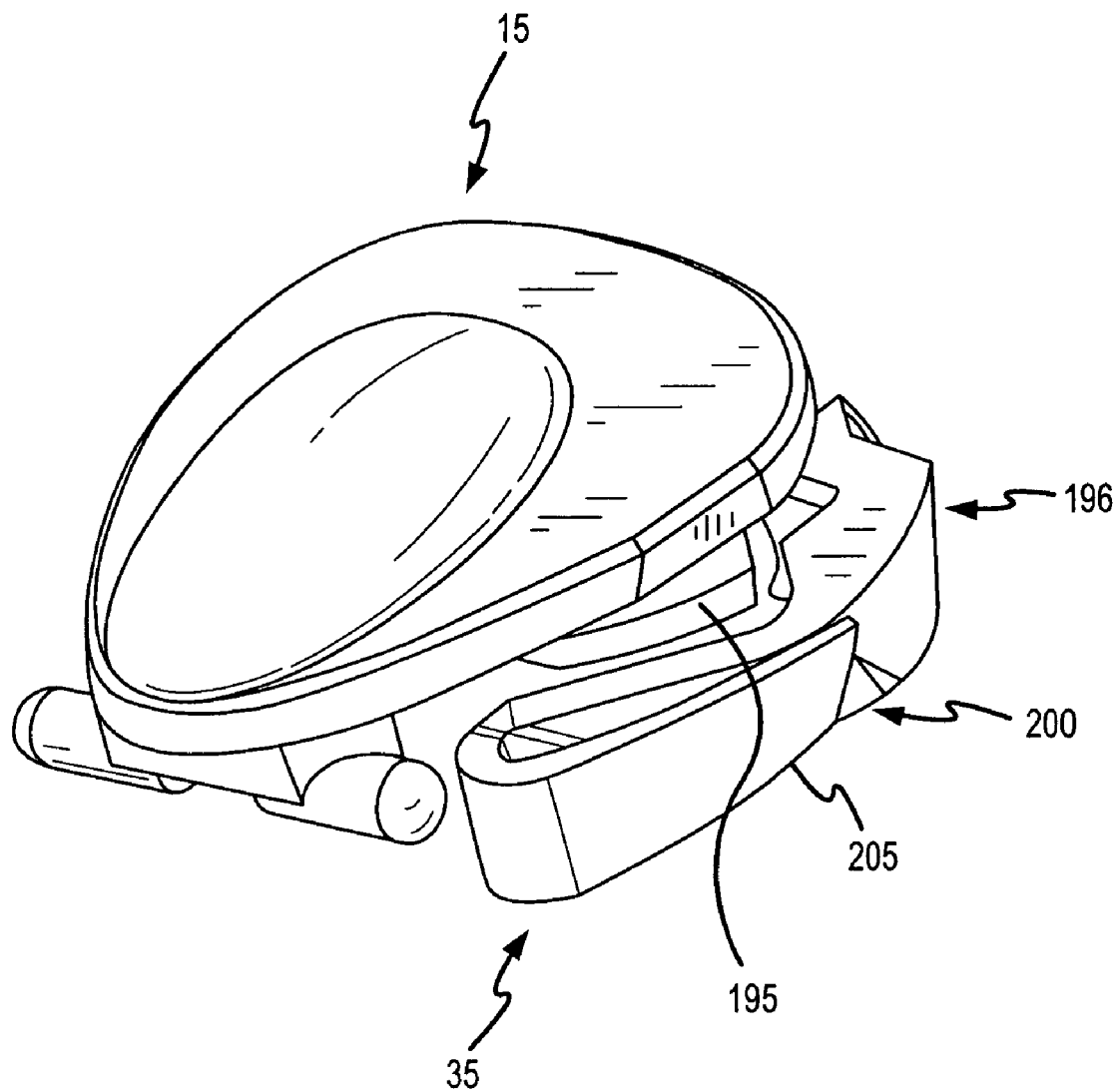
FIG. 14 is a top-rear isometric view of the relationship between the button and collet finger.
Figure 15:
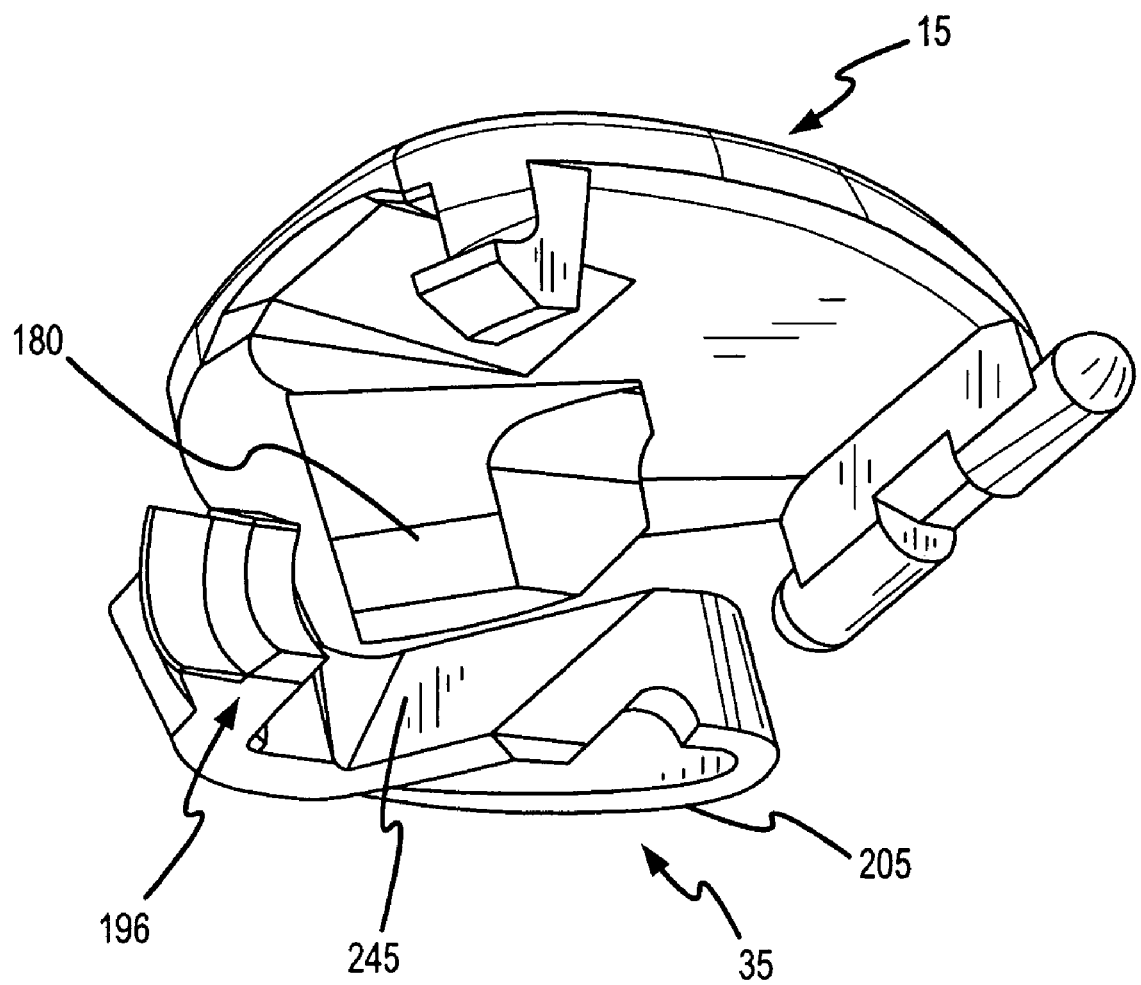
FIG. 15 is a bottom-front isometric view of the relationship between the button and collet finger.
Figure 28:
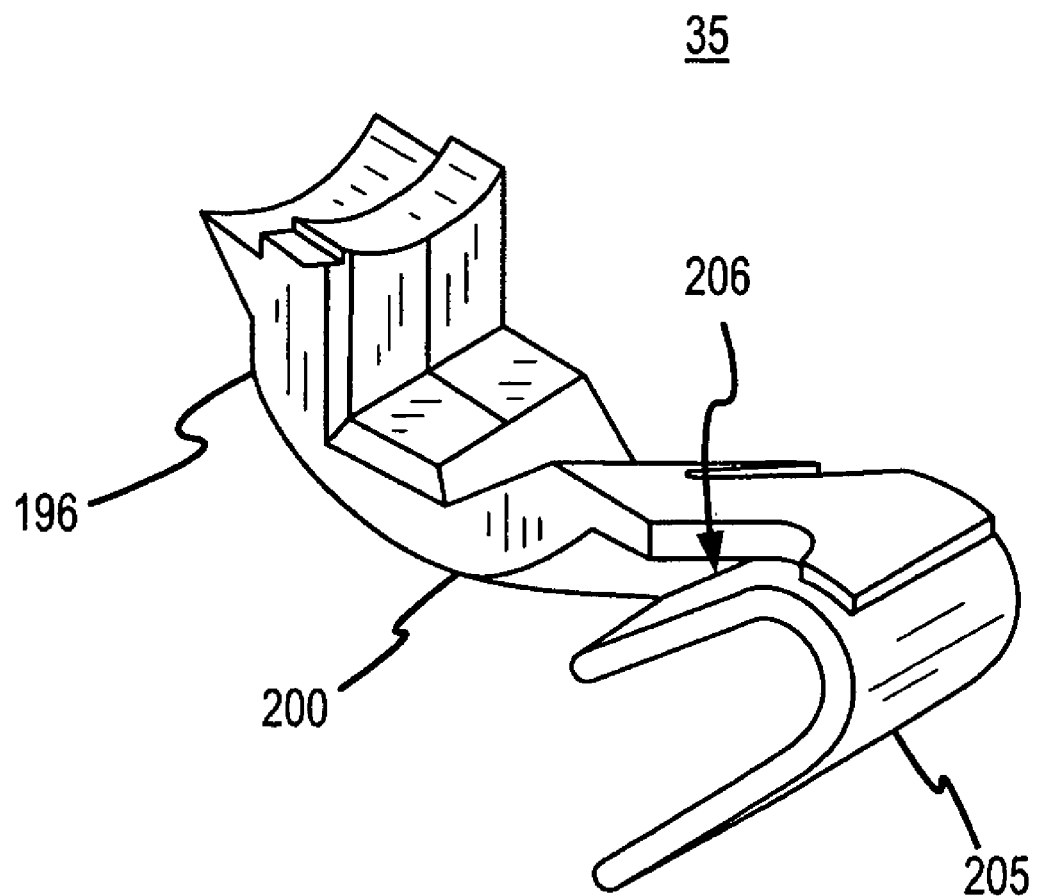
FIG. 28 is a bottom-rear isometric view of an alternative embodiment of the collet finger.
Figure 29:
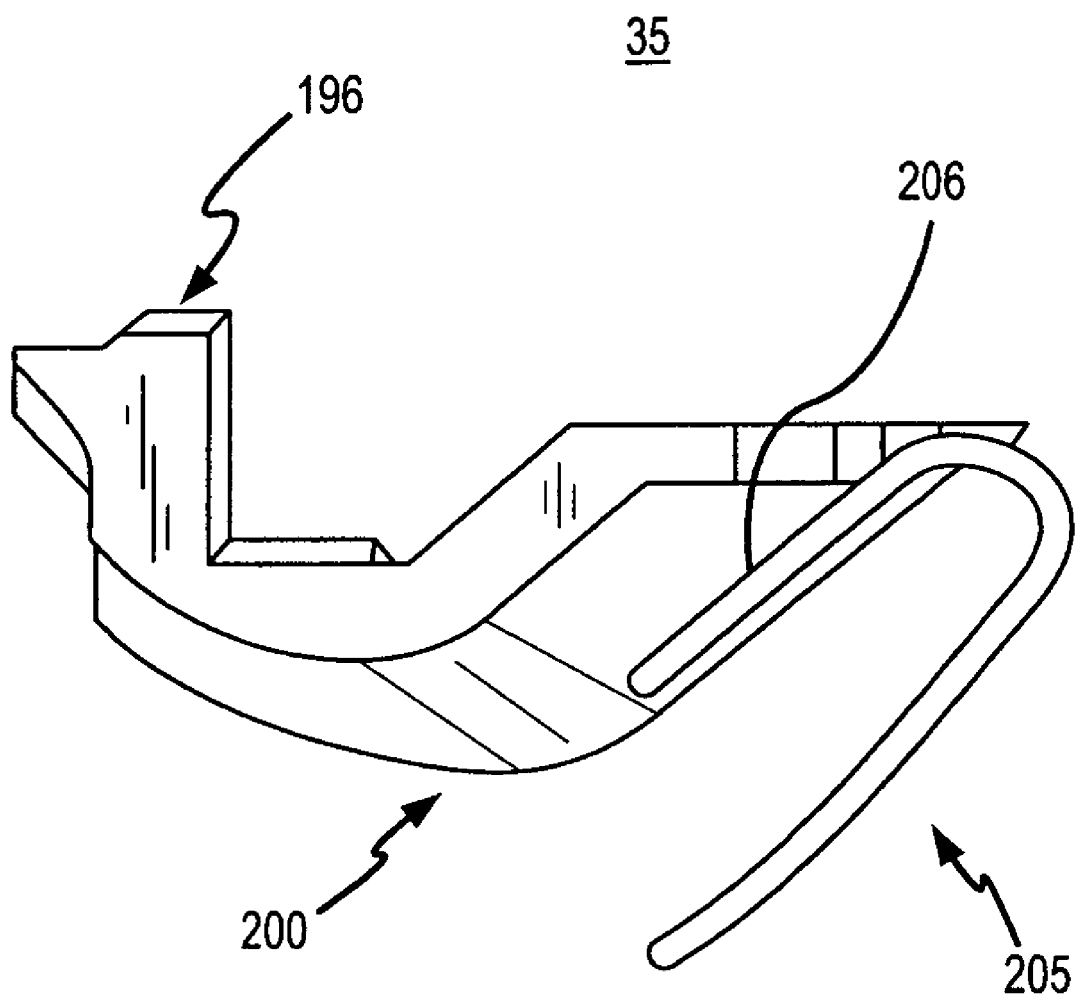
FIG. 29 is a bottom plan view of the embodiment of the collet finger depicted in FIG. 28.
Figure 30:
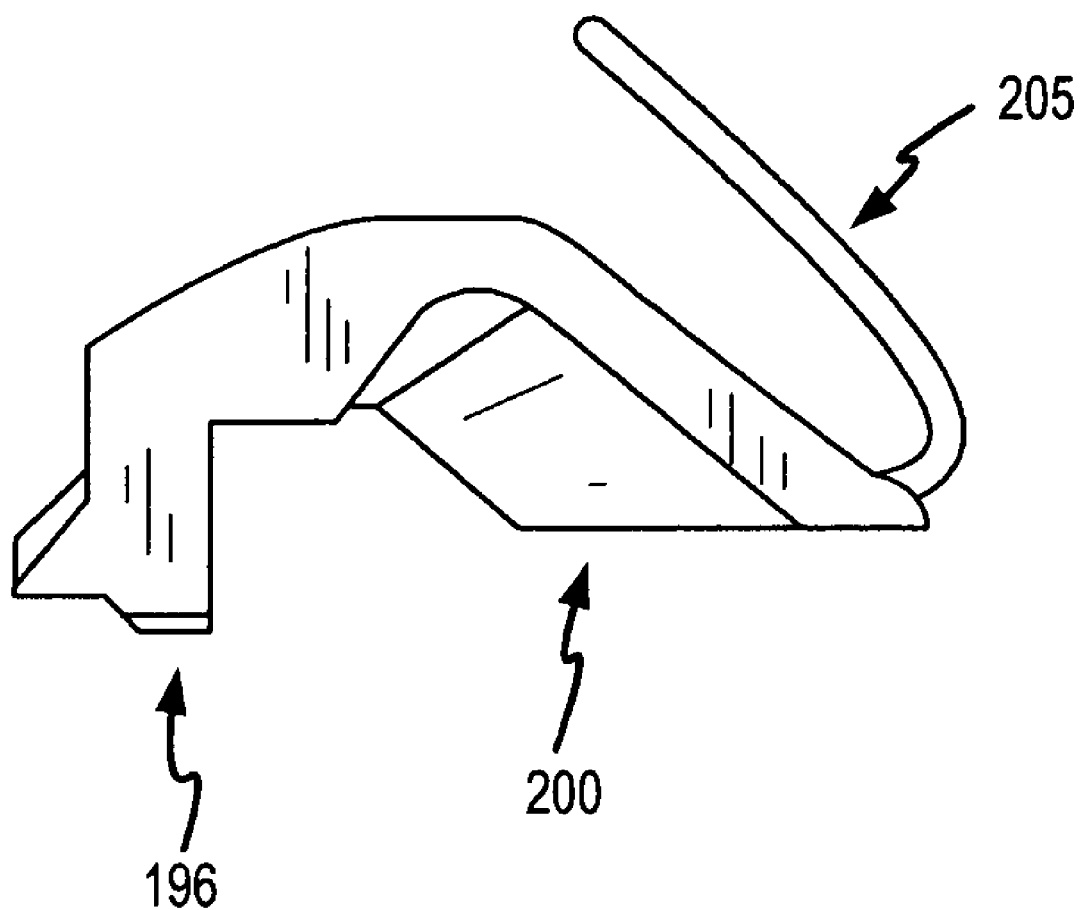
FIG. 30 is a top plan view of the embodiment of the collet finger depicted in FIG. 29.

For a discussion of the features of the collet finger 35, reference is now made to FIGS. 2, 11-16, and 28-30. FIG. 11 is top-rear isometric view of the collet finger 35. FIG. 12 is a bottom-front isometric view of the collet finger 35. FIG. 13 is a top-front isometric view of the collet finger 35. FIG. 14 is a top-rear isometric view of the relationship between the button 15 and collet finger 35. FIG. 15 is a bottom-front isometric view of the relationship between the button 15 and collet finger 35. FIG. 16 is a horizontal cross section of the male connector 10 coupled with the female coupler 5, as taken along section line AA in FIG. 1A. FIG. 28 is a bottom-rear isometric view of an alternative embodiment of the collet finger 35. FIG. 29 is a bottom plan view of the embodiment of the collet finger 35 depicted in FIG. 28. FIG. 30 is a top plan view of the embodiment of the collet finger 35 depicted in FIG. 29.

As shown in FIGS. 2 and 11-16, the collet finger 35 includes a head portion 196, a body portion 200, and a tail portion 205. The head portion 196 includes an engagement feature 210 configured to engage the groove 100 of the male connector 10. In one embodiment, the engagement feature 210 includes an arcuate leading edge 215, a first arcuate wall portion 220, an arcuate beveled surface 225, a second arcuate wall portion 230 and an arcuate lip 235. The first arcuate wall portion 220 extends from the arcuate leading edge 215 to the arcuate beveled surface 225. The second arcuate wall portion 230 extends from the arcuate beveled surface 225 to the arcuate lip 235. The arcuate leading edge 215 and first arcuate wall portion 220 are defined by a first radius. The arcuate lip 235 and the second arcuate wall portion 230 are defined by a second radius that is smaller than the first radius. The arcuate lip 235 is formed by the edge formed between the second arcuate wall portion 230 and a back planar surface 240 perpendicularly intersecting the second arcuate wall portion 230.

As shown in FIG. 16, when the grooved male end 55 of the male connector 10 is fully received within the opening 80 of the female coupler 5 such that the male connector 10 is coupled with the female coupler 5, the second arcuate wall portion 230 abuts against the recessed cylindrical segment 100''' of the groove 100. As a result, the arcuate lip 235 resides in the groove 100 adjacent to the leading beveled edge 100', thereby preventing the male connector 10 from being withdrawn from the female coupler 5.

As shown in FIGS. 2 and 11-16, the body portion 200 includes an arcuate inclined face 245 and a notch 250. The notch 250 is located on a bottom side of the body portion 200 and is configured to mate with features in the lower housing portion 25. The arcuate inclined face 245 is located on an inner side of the body portion 200 and tapers as it extends from the top of the body portion 200 to the bottom of the body portion 200. As can be understood from FIGS. 14-16, the arcuate inclined face 245 is configured to be engaged by the arcuate inclined surface 195 of the tapered wedge member 180.

As shown in FIG. 16, when the button 15 is not depressed, the tapered wedge member 180 does not wedge against the arcuate inclined face 245 of the body portion 200. As a result, the engagement feature 210 is not disengaged from the coupling feature (i.e., groove 100) of the male connector 5. However, when the button 15 is depressed, the tapered wedge member 180 wedges against the arcuate inclined face 245 of the body portion 200. Consequently, the engagement feature 210 is forced away (i.e., disengaged) from the coupling feature of the male connector 5.

As shown in FIGS. 2 and 11-16, in one embodiment, the collet finger 35 includes a tail portion 205 that curves back about the outside surface of the body portion 200. The tail portion 205 serves as an integral biasing element that acts against the interior surface of the lower housing portion 25 to bias the engagement feature 210 laterally inward towards the longitudinal axis of the fluid conduit 137 of the longitudinally extending body 112 of the female coupler 5. Thus, the biasing nature of the tail portion 205 causes the engagement feature 210 to remain in engagement with the coupling feature (i.e., groove 100) of the male connector 10 until caused to disengage by the actuation of the button 15.

In the embodiment depicted in FIGS. 2 and 11-16, the head, body and tail portions 196, 200, 205 are formed entirely from the same material in one piece. In one embodiment, the entire collet finger 35 is formed from nylon. In another embodiment, the entire collet finger 35 is formed from acetal. In yet other embodiments, the entire collet finger 35 is formed from other appropriate polymers.

In one embodiment, as indicated in FIGS. 28-30, the integral biasing element 205 of the collet finger is formed from a material that is dissimilar from the material used to form the rest of the collet finger 35. Specifically, the head and body portions 196, 200 are formed from a polymer and the tail portion 205 is formed from a metal such as 302 stainless steel. As can be understood from FIGS. 28-30, the biasing element 205 is a leaf spring 205 received in a slot 206 in the body portion 200 of the collet finger 35.

In one embodiment, the integral biasing element 205 is replaced with a biasing element 205 that is separate from the collet finger 35. In one such embodiment, the separate biasing element 205 is a leaf spring located between a surface of the collet finger 35 and the interior surface of the housing 12. In one embodiment, the separate biasing element 205 is a helical spring located between a surface of the collet finger 35 and the interior surface of the housing 12.

As can be understood from FIG. 16, when the male connector 10 is inserted into the opening 80 of the female coupler 5, the beveled edge 110 of the tip of the grooved male end 55 of the male connector 10 interacts with the arcuate beveled surface 225 of the engagement feature 210 to cause the engagement feature 210 to displace laterally away from the male connector 10 (i.e., the engagement feature 210 displaces generally perpendicularly away from the travel direction of the male connector 10 as the male connector 10 travels through the opening 80 of the female coupler 5). Once the male connector 10 is fully inserted into the female coupler 5, the biasing nature of the tail 205 causes the engagement feature 210 to displace laterally back towards male connector 10 such that the arcuate lip 235 is received within the groove 100 of the male connector 10.

As indicated in FIG. 16, when the male connector 10 is fully inserted in the female coupler 5, the cylindrical rim 105 of the male grooved end 55 of the male connector 5 is received within the stepped opening 160 of the female end 135. As a result, the cylindrical rim 105 abuts against the inner circumferential surface of the o-ring 45 to form a liquid tight seal.

In one embodiment, the o-ring 45 is formed from nitrile buna-n. In other embodiments, the o-ring 45 is formed from other appropriate polymer materials.

e. Lower Housing Portion

Figure 17:
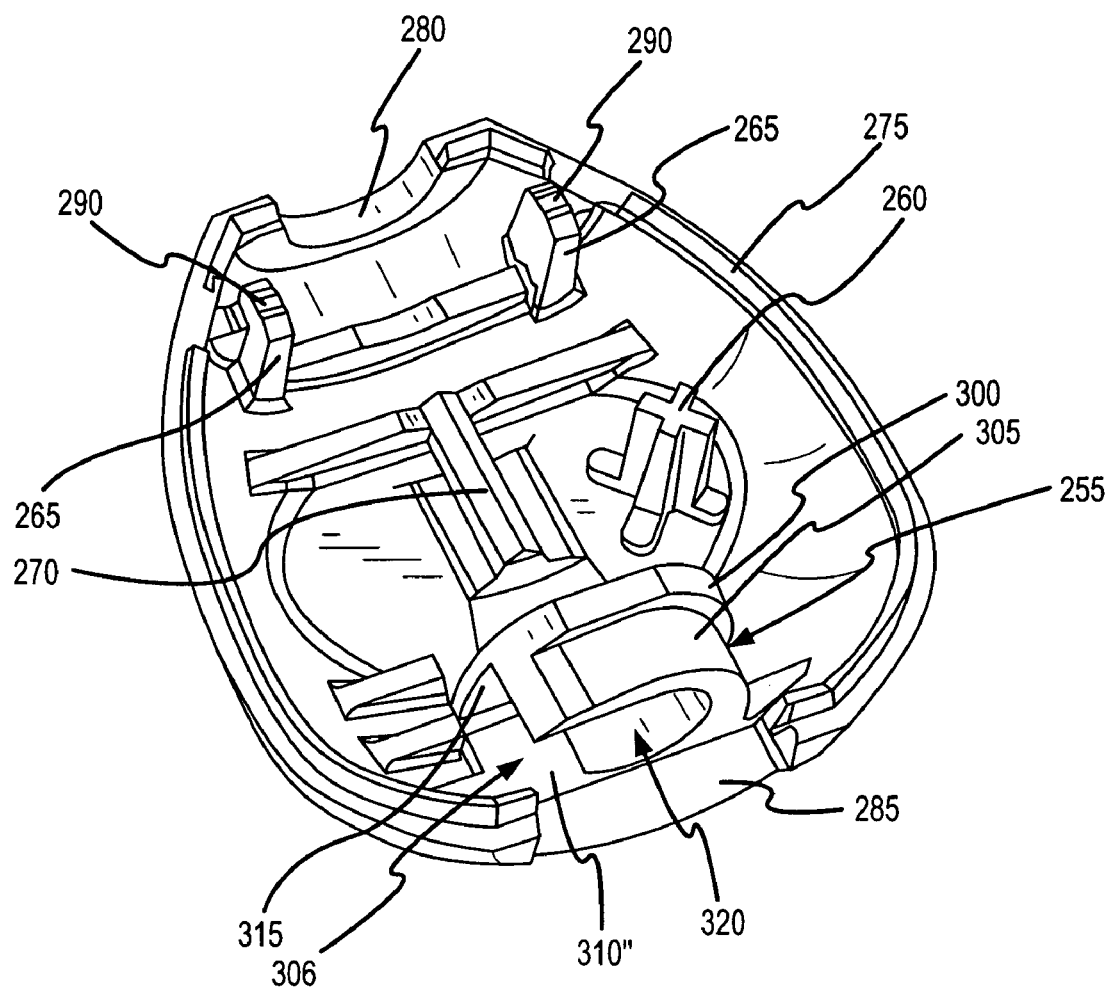
FIG. 17 is top-front isometric view of the lower housing portion.
Figure 18:
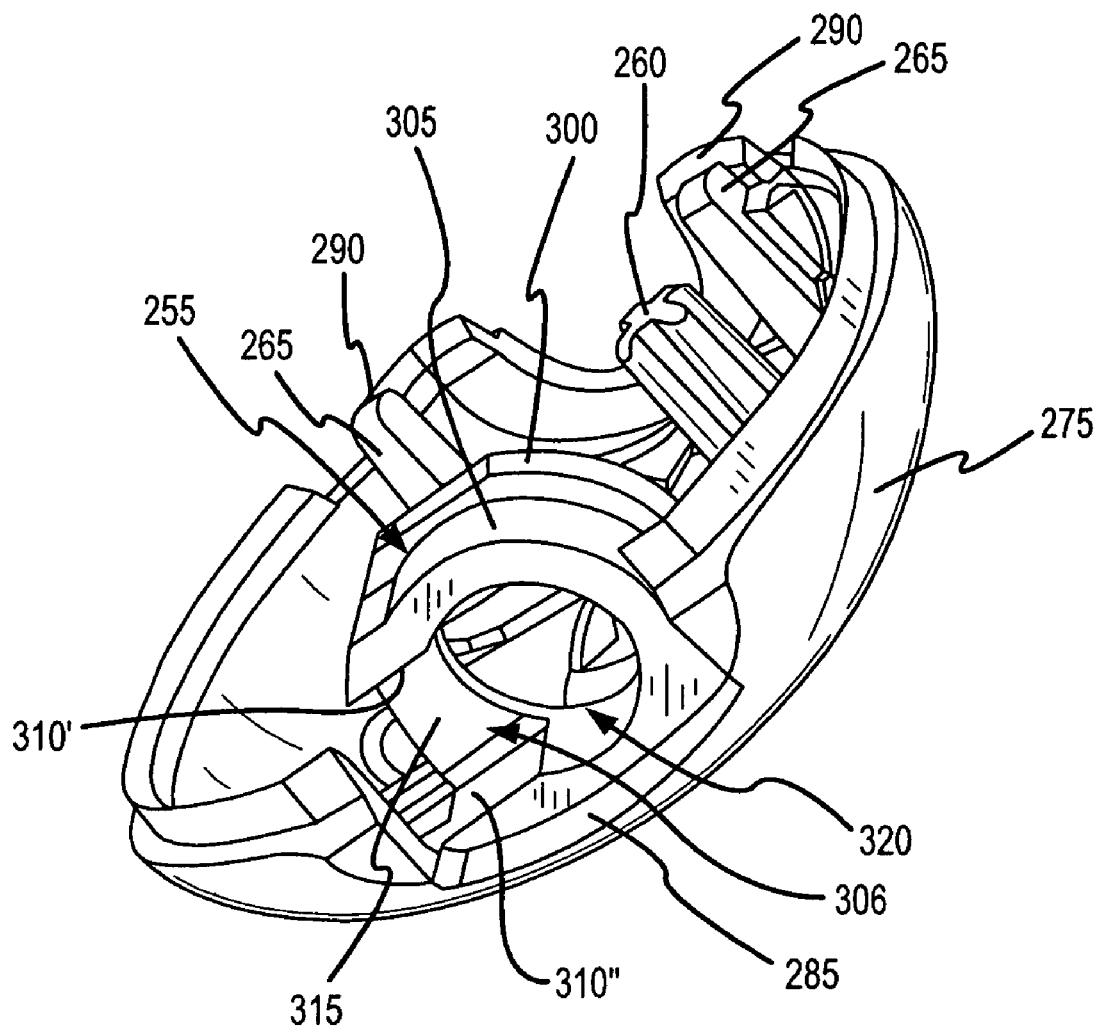
FIG. 18 is another top-front isometric view of the lower housing portion.
Figure 19:
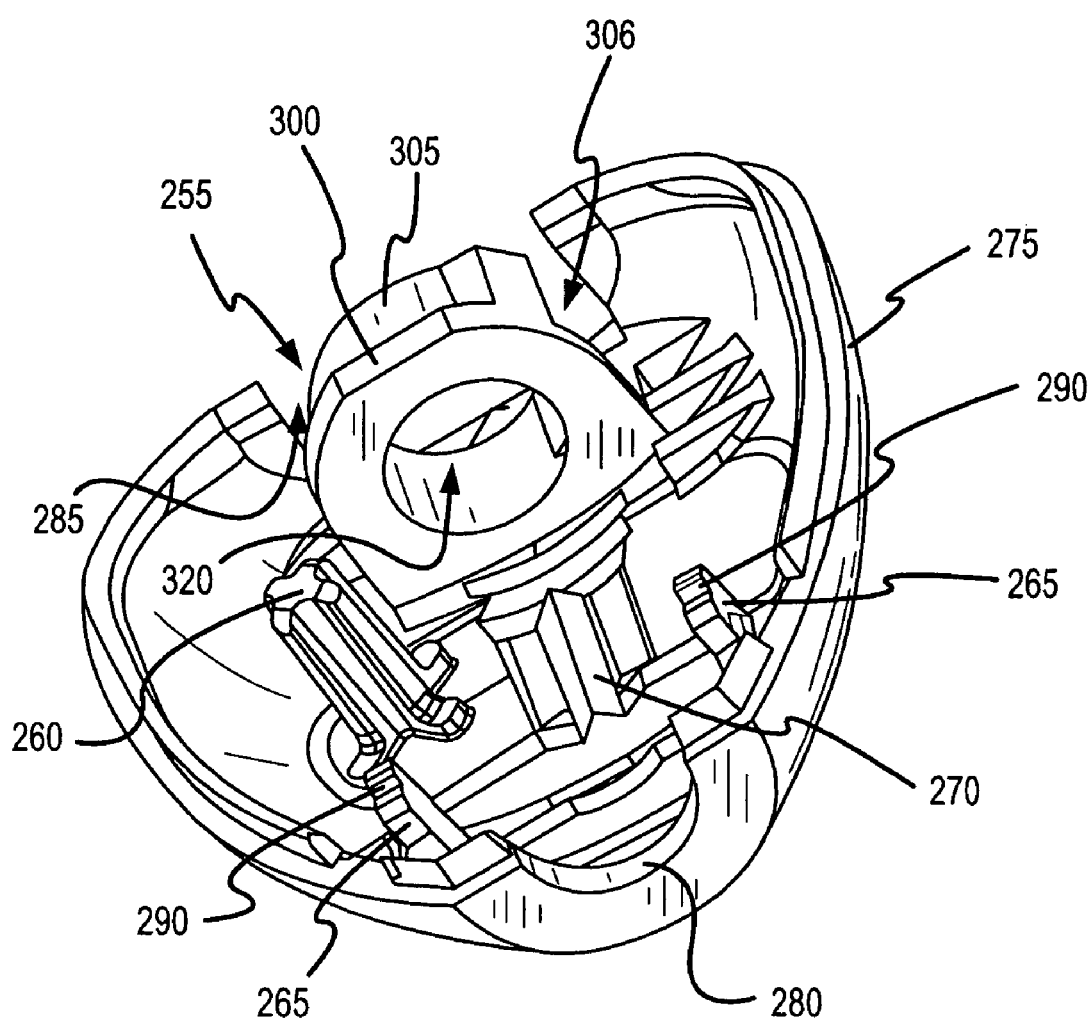
FIG. 19 is a top-rear isometric view of the lower housing portion.
Figure 20:
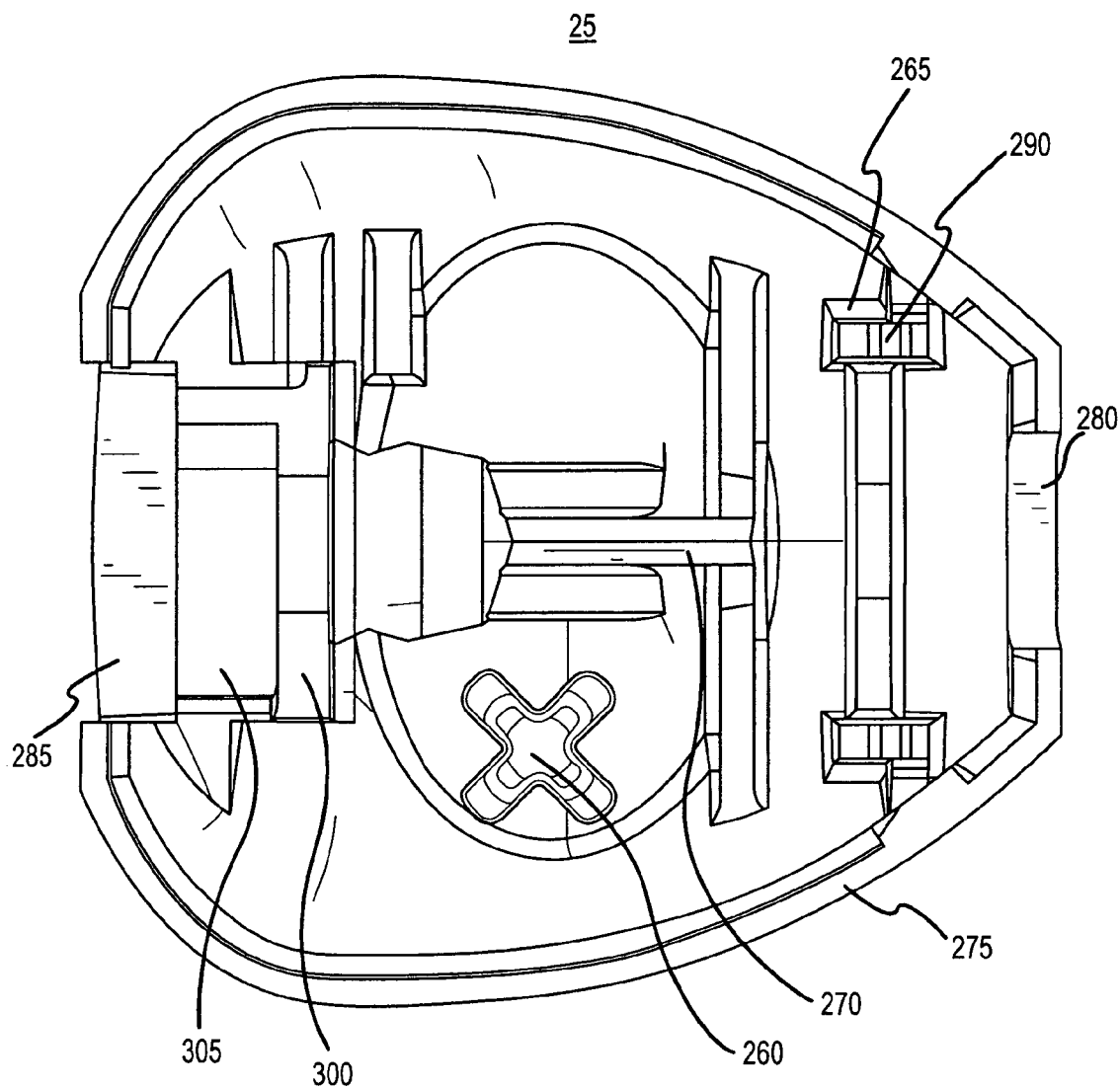
FIG. 20 is a top plan view of the lower housing portion.
Figure 21:
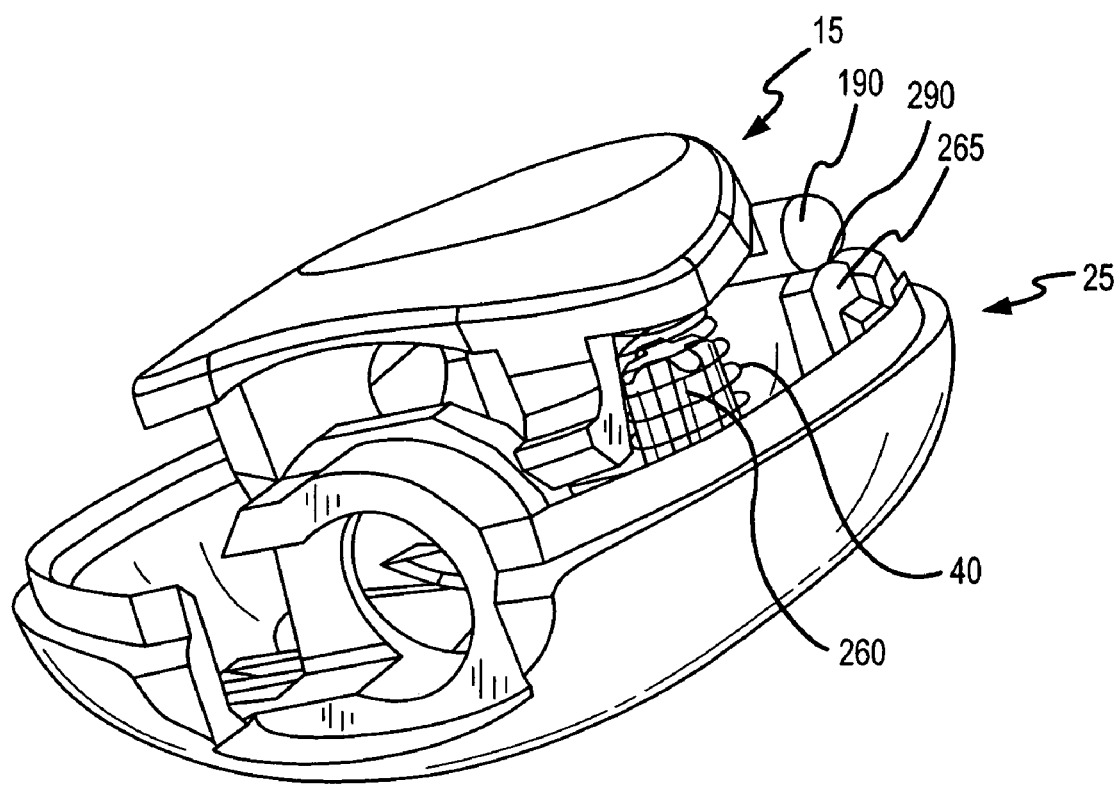
FIG. 21 is a top-front isometric view of the relationship between the button and lower housing portion.
Figure 22:
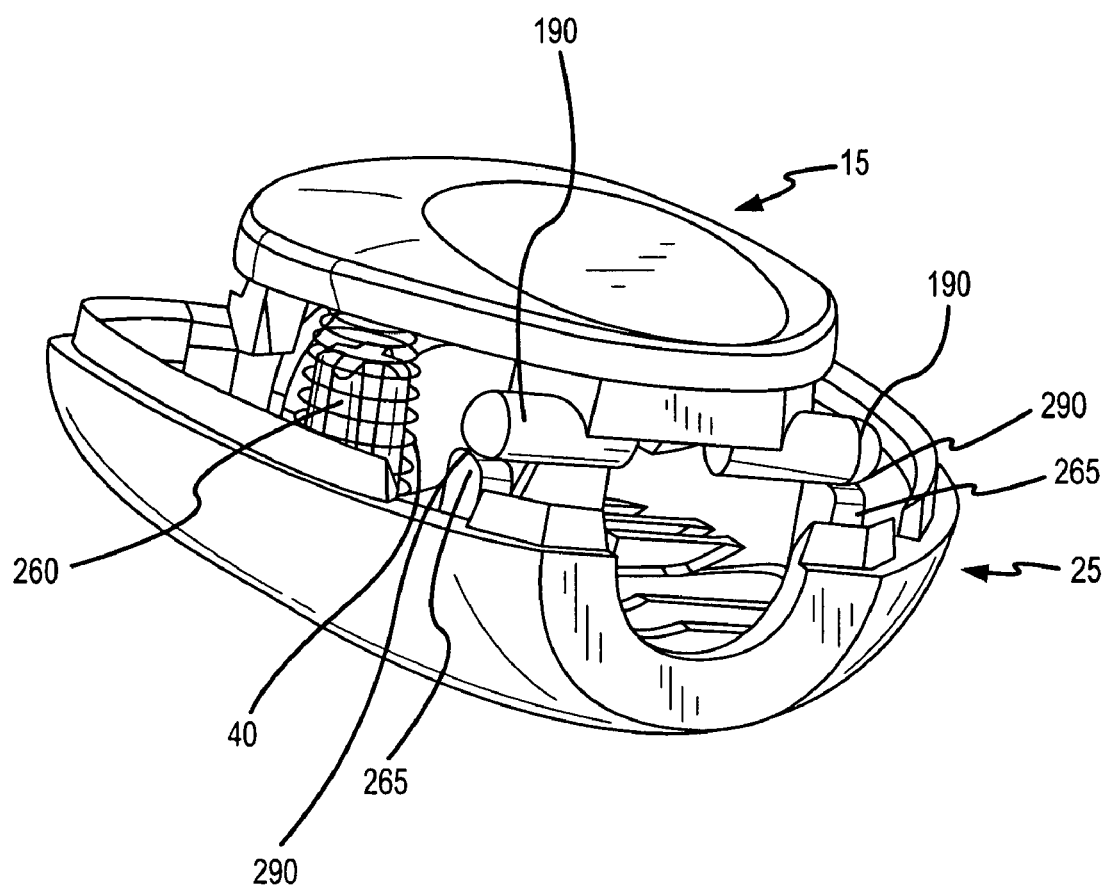
FIG. 22 is a top-rear isometric view of the relationship between the button and lower housing portion.
Figure 23:
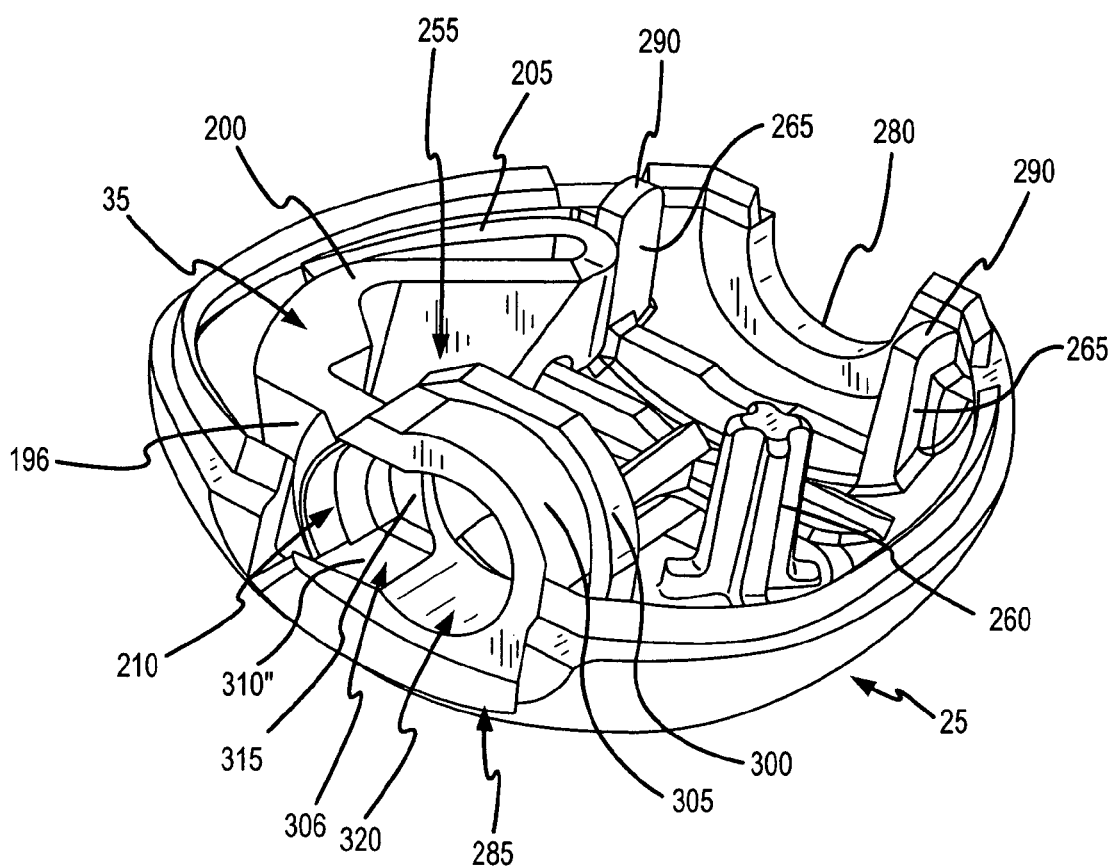
FIG. 23 is a top-front isometric view of the relationship between the collet finger and lower housing portion.
Figure 24:
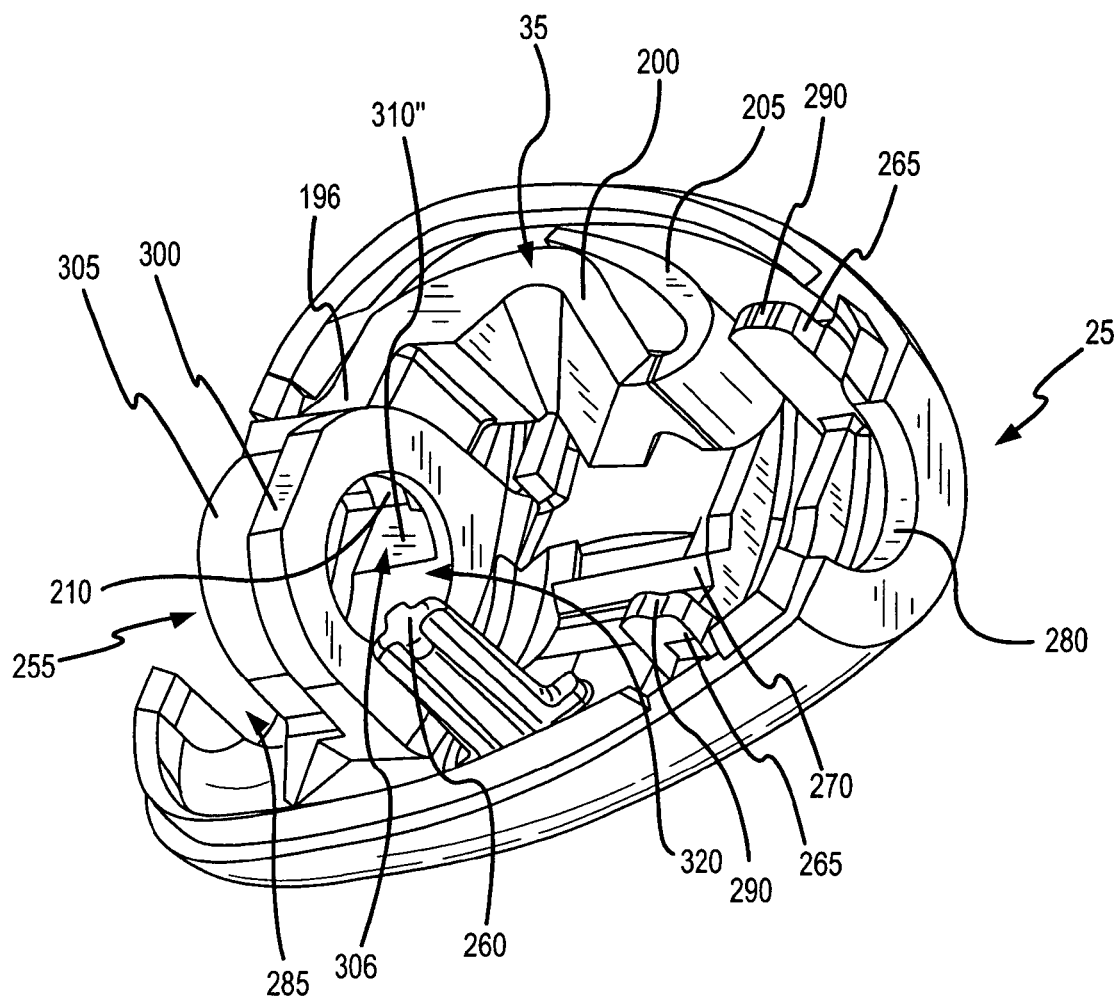
FIG. 24 is a top-rear isometric view of the relationship between the collet finger and lower housing portion.

For a discussion of the features of the lower housing portion 25, reference is now made to FIGS. 2 and 17-24. FIG. 17 is top-front isometric view of the lower housing portion 25. FIG. 18 is another top-front isometric view of the lower housing portion 25. FIG. 19 is a top-rear isometric view of the lower housing portion 25. FIG. 20 is a top plan view of the lower housing portion 25. FIG. 21 is a top-front isometric view of the relationship between the button 15 and lower housing portion 25. FIG. 22 is a top-rear isometric view of the relationship between the button 15 and lower housing portion 25. FIG. 23 is a top-front isometric view of the relationship between the collet finger 35 and lower housing portion 25. FIG. 24 is a top-rear isometric view of the relationship between the collet finger 35 and lower housing portion 25.

As shown in FIGS. 2 and 17-20, the lower housing portion 25 includes a collar 255, a spring post 260, a pair of saddle posts 265, a ridge 270, a shell wall 275, a semi-circular opening 280, and a rectangular opening 285. The ridge 270 is centered laterally within the interior of lower housing portion 25 and extends longitudinally in a manner that is parallel to the longitudinal axis of the lower housing portion 25. The ridge 270 mates with the pair of parallel ribs 165 extending longitudinally along the bottom surface of the body 112 of the upper housing portion 20.

As can be understood from FIGS. 1C and 17-20, the exterior surface of the shell wall 275 is rounded and ergonomically shaped. The interior surface of the shell wall 275 defines a bowl-like volume. The semi-circular opening 280 in the rear of the shell wall 275 receives the longitudinally extending body 112 of the upper housing portion 20 when the upper and lower housing portions 20, 25 are mated together to form the overall housing 12, as can be understood from FIG. 1D. The rectangular opening 285 in the front of the shell wall 275 receives the front housing portion 30, as discussed later in this Detailed Description.

As illustrated in FIGS. 2 and 17-20, the spring post 260 extends generally vertically upward from the interior surface of the shell wall 275. As shown in FIGS. 21 and 22, the helical spring 40 is centered about the spring post 260 and acts against the bottom surface of the button platform 174 to bias the button 15 upward into a position wherein the wedge element 180 does not engage the collet finger 35.

As indicated in FIGS. 2 and 17-20, each saddle post 265 includes an arcuate saddle surface 290. As shown in FIGS. 21 and 22, each arcuate saddle surface 290 serves as another lower half of a pivot pin bracket for retaining a pivot pin 190 of the button 15, thereby allowing the button 15 to pivot relative to the lower housing portion 25.

As illustrated in FIGS. 2 and 17-20, the collar 255 includes a flange 300 perpendicularly intersecting a cylindrical wall portion 305. A window 306 or opening extends laterally through the cylindrical wall portion 305 and is defined in the cylindrical wall portion 305 by upper and lower planar wall portions 310',310". The front side of the window 306 is open, and the rear side 315 of the window 306 is the vertical planar face of the flange. A cylindrical opening 320 passes through the collar 255. Thus, as can be understood from FIG. 16, when the male connector 10 is fully inserted into the female coupler 5, the grooved male end 55 passes through the cylindrical opening 320 to be received in the stepped opening 160 of the female end 135 of the body 112 of the upper housing portion 20.

As indicated in FIGS. 16, 23 and 24, the upper and lower planar surfaces of the head 196 of the collet finger 35 slidably abut against the upper and lower planar wall portions 310', 310" of the window 306. As a result, the head 196 of the collet finger 35 may extend into or retract out of the cylindrical opening 320 via the window 306, thereby allowing the engagement feature 210 of the collet finger 35 to move into or out of engagement with the coupling feature 100 of the male connector 100.

In one embodiment, the lower housing portion 25 is formed from acrylonitrile-butadiene-styrene ("ABS"). In another embodiment, the lower housing portion 25 is formed from polycarbonate. In yet other embodiments, the lower housing portion 25 is formed from other appropriate polymers.

f. Front Housing Portion

Figure 25:
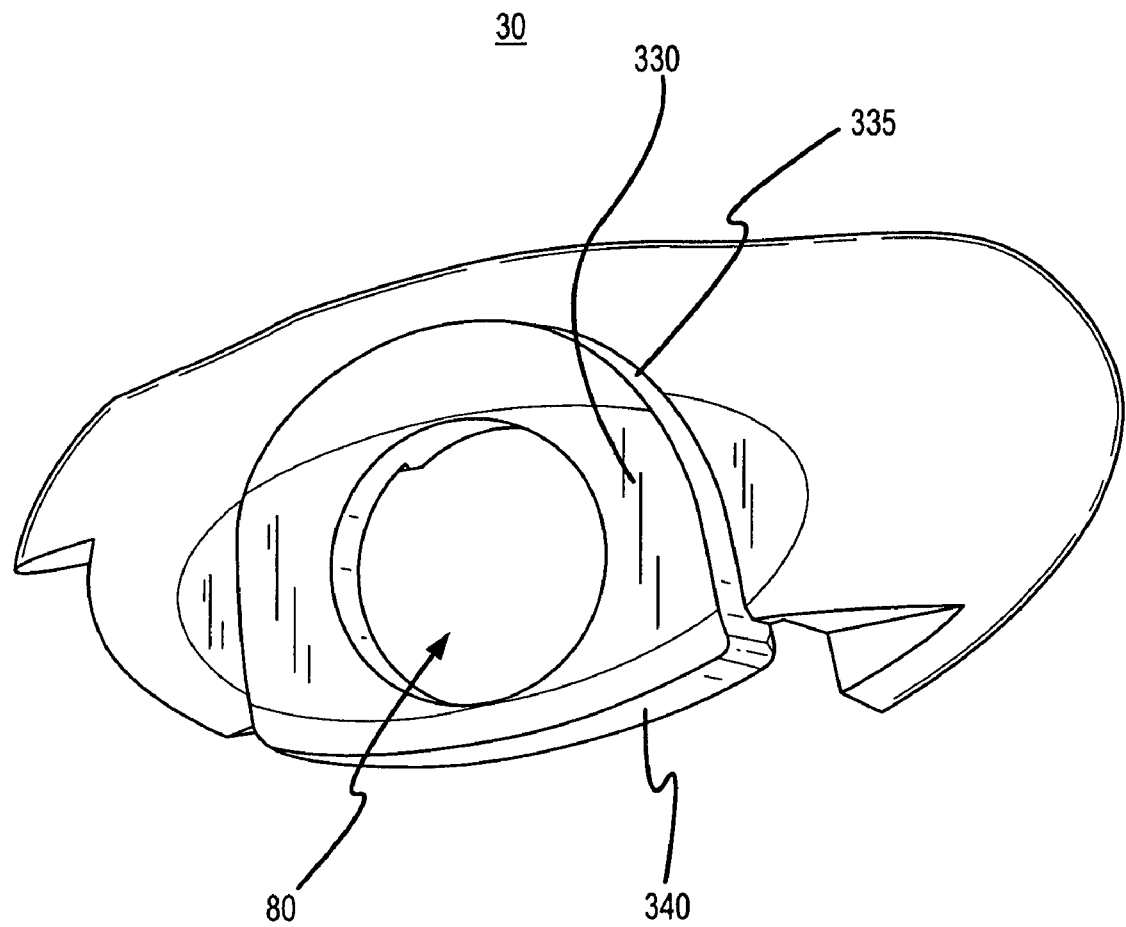
FIG. 25 is bottom-front isometric view of the front housing portion.
Figure 26:
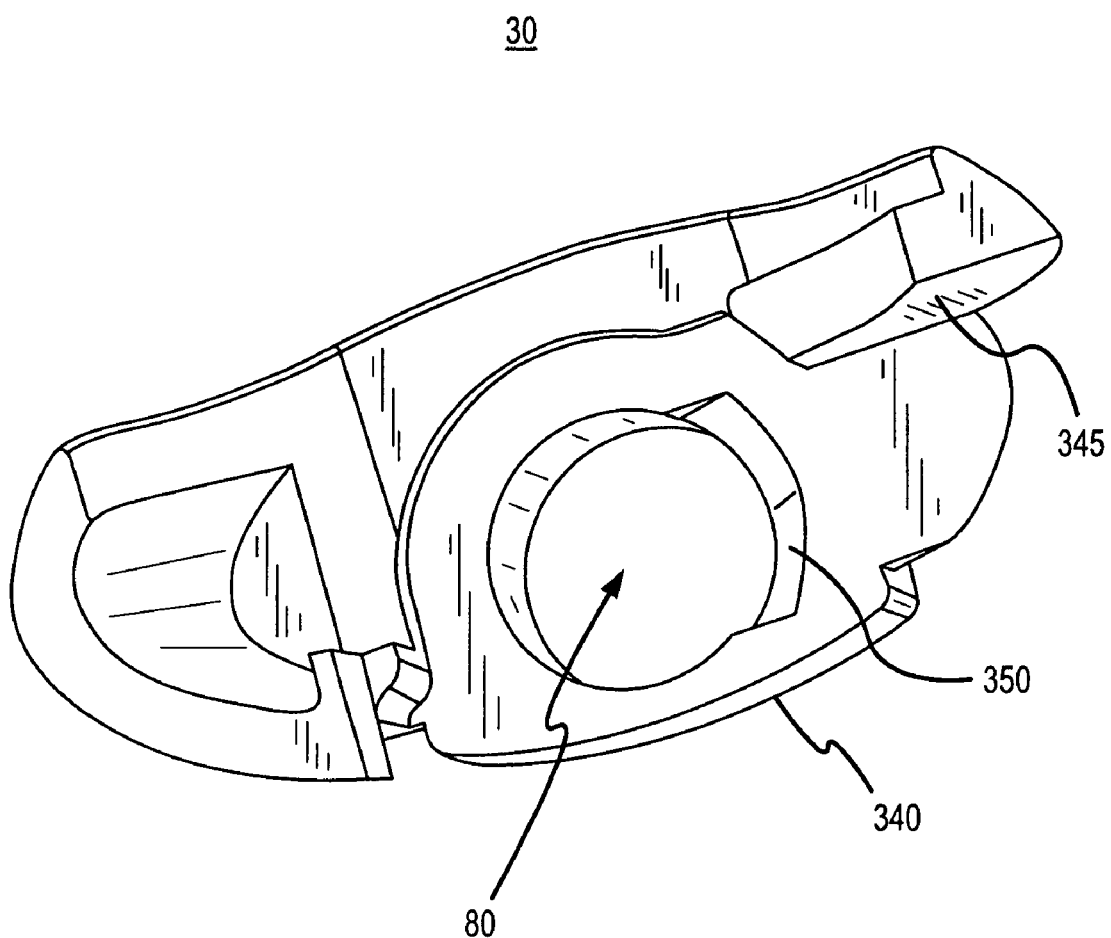
FIG. 26 is a bottom-rear isometric view of the front housing portion.

For a discussion of the features of the front housing portion 30, reference is now made to FIGS. 1B, 1C, 2, 16, 25 and 26. FIG. 25 is bottom-front isometric view of the front housing portion 30. FIG. 26 is a bottom-rear isometric view of the front housing portion 30. As shown in FIG. 25, the front of the front housing portion 30 includes an extended face 330 that has a semi-circular upper section 335, a rectangular lower section 340 and an opening 80 extending through the extended face 330. As can be understood from FIGS. 1B, 1C and 2, the semi-circular upper section 335 is received by the semi-circular opening 115 in the shell wall 110 of the upper housing portion 20, and the rectangular lower section 340 is received by the rectangular opening 285 in the shell wall 275 of the lower housing portion 25.

As can be understood from FIG. 16, the opening 80 in the extended face 330 leads to the opening 320 in the collar 255 of the lower housing portion 25. Thus, the two openings 80, 320 combine to guide the male connector 10 into proper alignment with the female coupler 5 as the male connector 10 passes into the female coupler 5.

As indicated in FIG. 26, the rear of the front housing portion 30 includes an overhanging ledge 345, which serves as an upper planar surface against which the upper planar surface of the collet finger 35 slidably displaces. The inner edge of the opening 80 adjacent the ledge 345 is tapered. This tapered edge 350 facilitates the engagement of the engagement feature 210 of the collet finger 35 with the coupling feature 100 of the male connector.

In one embodiment, the front housing portion 30 is formed from acrylonitrile-butadiene-styrene ("ABS"). In another embodiment, the front housing portion 30 is formed from polycarbonate. In yet other embodiments, the front housing portion 30 is formed from other appropriate polymers.

e. Coupler Operation

Figure 27:
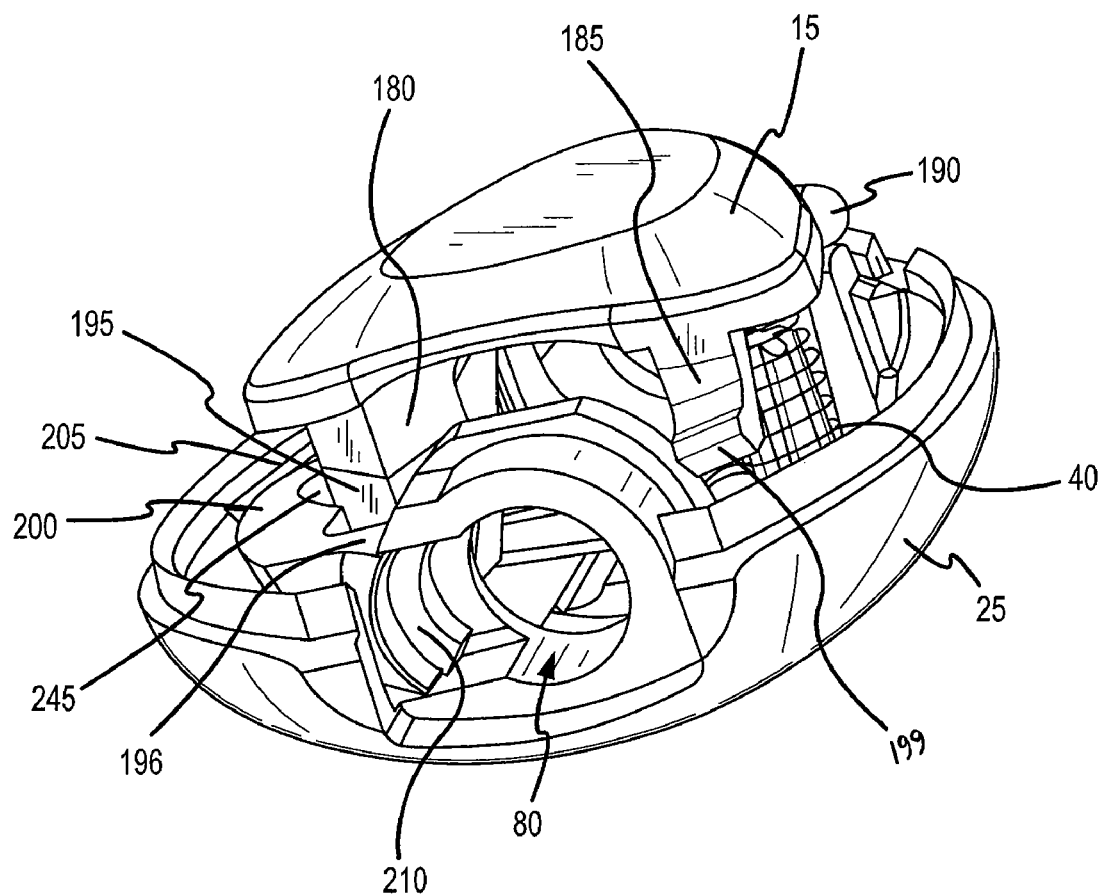
FIG. 27 is a top-front isometric view of the relationship between the collet finger, button and lower housing portion.

For a discussion on the operation of the female coupler 5, reference is now made to FIGS. 1A, 2, 16 and 27. FIG. 27 is a top-front isometric view of the relationship between the collet finger 35, button 15 and lower housing portion 25. As can be understood from FIGS. 1A, 2, 16 and 27, in order to couple the male connector 10 with the female coupler 5, the male grooved end 55 of the male connector 10 is aligned with the opening 80 of the female coupler 5 and then inserted. As the grooved male end 55 proceeds through the openings 80, 320, the beveled leading edge 110 of the grooved male end 55 encounters the beveled arcuate surface 225 of the engagement feature 210 of the collet finger 35. This encounter causes the head 196 of the collet finger 35 to displace within the window 306 in a lateral direction away from the grooved male end 55 and against the biasing force of the biasing element 205 of the collet finger 35. As the cylindrical rim 105 of the grooved male end 55 is fully received in the stepped opening 160 of the female end 135 of the body 112 of the upper housing portion 20, the arcuate edge 235 of the engagement feature 210 slips past the leading beveled edge 100' of the groove 100 to fall into the groove 100. As a result, the engagement feature 210 engages the coupling feature 100 and the female coupler 5 couples with the male connector 10.

As can be understood from FIGS. 1A, 2, 16 and 27, in order to decouple the male connector 10 from the female coupler 5, the button 15 is depressed against the upward biasing force of the helical spring 40 to pivot about the pivot pins 190 into the button opening 120 in the top surface of the housing 12. This drives the tapered wedge member 180 downward, which forces the arcuate inclined surface 195 of the wedge member 180 against the arcuate inclined face 245 of the collet finger 35. As a result, the collet finger 35 is driven against the biasing element 205 of the collet finger 35 and laterally away from the longitudinal axis of the female coupler 5. This causes the engagement feature 210 of the collet finger 35 to disengage from the coupling feature 100 of the male connector 10. While the engagement feature 210 and coupling feature 100 are disengaged, the male connector 10 is withdrawn from opening 80 of the female coupler 5.

Although the present invention has been described with reference to preferred embodiments, persons skilled in the art will recognize that changes may be made in form and detail without departing from the spirit and scope of the invention. The invention is limited only by the scope of the following claims.

What is claimed is:

1. A connector system for releasably coupling together first and second fluid conduits, the connector system comprising:
    a male connector including:
        a first end configured to operably couple with the first fluid conduit;
        a second end including a coupling feature; and
        a fluid conduit extending between the first and second ends of the male connector; and
    a female connector including:
        a first end configured to operably couple with the second fluid conduit;
        a second end including an opening configured to receive therein the second end of the male connector when the male and female connectors are releasably coupled, wherein the opening guides the second end of the male connector along a first line of action as the second end of the male connector is received into the opening;
        a fluid conduit extending between the first and second ends of the female connector;
        an engagement member including an engagement feature, wherein the engagement feature displaces along a second line of action generally normal to the first line of action when the second end of the male connector is received in the opening, the engagement feature engaging the coupling feature to releasably couple the male connector to the female connector; and
        an actuation element that displaces along a third line of action generally normal to the first and second lines of action in order to disengage the engagement feature from the coupling feature.

2. The connector system of claim 1, wherein the female connector further includes a button from which the actuation element extends.

3. The connector system of claim 2, wherein the female connector further includes a housing and wherein the button is pivotally coupled to the housing.

4. The connector system of claim 2, wherein the female connector further includes a housing substantially enclosing the engagement member and supporting the button.

5. The connector system of claim 2, wherein the female connector further includes first and second biasing elements, the first biasing element acting against the engagement member to bias the engagement feature into engagement with the coupling feature, the second biasing element acting against the button to bias the actuation element away from the engagement member.

6. The connector system of claim 1, wherein when the second end of the male connector is fully received in the opening, the fluid conduits of the male and female connectors are placed in fluid communication.

* * * * *